United States Patent [19]

De et al.

[11] Patent Number: 5,672,598
[45] Date of Patent: Sep. 30, 1997

[54] LACTAM-CONTAINING HYDROXAMIC ACIDS

[75] Inventors: Biswanath De, Cincinnati; Christopher Thomas Wahl, Hamilton; Michael George Natchus, Cincinnati; Menyan Cheng, West Chester, all of Ohio

[73] Assignee: The Procter & Gamble Company, Cincinnati, Ohio

[21] Appl. No.: 407,839

[22] Filed: Mar. 21, 1995

[51] Int. Cl.⁶ .......................... C07D 223/10; A61K 31/55
[52] U.S. Cl. .......................... 514/212; 540/528; 546/243; 548/550; 514/327; 514/424
[58] Field of Search .................. 540/528; 546/243; 548/550; 514/212, 327, 424

[56] References Cited

U.S. PATENT DOCUMENTS

| | | | |
|---|---|---|---|
| 4,743,587 | 5/1988 | Dickens et al. | 514/575 |
| 4,771,038 | 9/1988 | Wolanin et al. | 514/18 |
| 4,918,105 | 4/1990 | Cartwright et al. | 514/575 |
| 4,996,358 | 2/1991 | Handa et al. | 562/621 |
| 5,075,302 | 12/1991 | Neustadt | 514/211 |
| 5,183,900 | 2/1993 | Galardy et al. | 560/42 |
| 5,189,178 | 2/1993 | Galardy et al. | 548/495 |
| 5,300,674 | 4/1994 | Crimmin et al. | 560/42 |
| 5,310,763 | 5/1994 | Campion et al. | 514/575 |
| 5,453,438 | 9/1995 | Campion et al. | 514/424 |

FOREIGN PATENT DOCUMENTS

| | | | |
|---|---|---|---|
| 2002-021-A | 11/1988 | Canada | A01N 37/30 |
| 0 231 081 | 8/1987 | European Pat. Off. | C07K 5/06 |
| 450-355-A | 4/1990 | European Pat. Off. | A01N 43/10 |
| 0 498 665 A1 | 8/1992 | European Pat. Off. | C07C 259/06 |
| 0 575 844 A2 | 12/1993 | European Pat. Off. | C07C 259/06 |
| 4127842A1 | 2/1993 | Germany | C07D 333/24 |
| 04217950-A | 8/1992 | Japan | C07C 259/06 |
| 2 268 934 | 1/1994 | United Kingdom | C07C 259/06 |
| 91/02716 | 3/1991 | WIPO | C07C 259/06 |
| 91/08737 | 6/1991 | WIPO | A61K 31/16 |
| 92/09563 | 6/1992 | WIPO | C07C 259/00 |
| 92/17460 | 10/1992 | WIPO | C07D 245/02 |
| 93/00082 | 1/1993 | WIPO | A61K 31/16 |
| 93/09090 | 5/1993 | WIPO | C07C 259/06 |
| 93/20047 | 10/1993 | WIPO | C07C 317/44 |
| 93/21942 | 11/1993 | WIPO | A61K 37/02 |
| 94/10990 | 5/1994 | WIPO | A61K 31/16 |

OTHER PUBLICATIONS

Johnson, W.H., N.A. Roberts and N. Borkakoti, "Collagenase Inhibitors: Their Design and Potential Therapeutic Use", J. Enzyme Inhibition, vol. 2, pp. 1–22, (No Month Identified 1987).

Odake, Sh., T. Okayama, M. Obata, T. Morikawa, S. Hattori, H. Hori and Y. Nagai, "Vertebrate Collagenase Inhibitor. II. Tetrapeptidyl Hydroxamic Acids", Chem. Pharm. Bull., vol. 39, No. 6, pp. 1489–1494 (Jun. 1991).

*Primary Examiner*—Robert T. Bond
*Attorney, Agent, or Firm*—David L. Suter; Richard A. Hake; Carl J. Roof

[57] ABSTRACT

The present invention relates to compounds that exhibit inhibitory activity against matrix metalloproteases ("MMPs"). Because MMPs are known to play a role in tissue degradation, the compounds of the present invention may be useful in preventing or treating diseases associated with excess MMP activity. In particular, the compounds have a structure according to Formula (I)

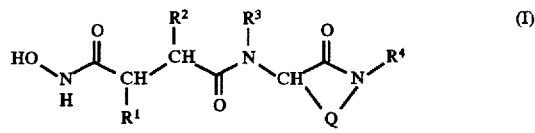

wherein $R^1$, $R^2$, $R^3$ and $R^4$ are various substituents as described in the specification; and Q is an alkyl chain, an alkenyl chain, a heteroalkyl chain, or a heteroalkenyl chain, wherein said chain has 2, 3, or 4 chain atoms and is unsubstituted or substituted with one or more alkyl moieties; or a pharmaceutically-acceptable salt, or biohydrolyzable alkoxyamide, acyloxyamide, or imide thereof. Preferred are those compounds where Q is an alkyl chain having 2, 3 or 4 chain atoms.

The invention also relates to pharmaceutical compositions comprising these compounds, and methods for preventing or treating diseases associated with unwanted MMP activity using the compounds and compositions.

2 Claims, No Drawings

LACTAM-CONTAINING HYDROXAMIC ACIDS

TECHNICAL FIELD

This invention is directed to compounds which are useful in treating diseases associated with excess and/or unwanted matrix metalloprotease activity, particularly collagenase and/or stromelysin activity. More specifically, the invention is directed to hydroxamic acid compounds that contain a substituted lactam ring.

BACKGROUND

A number of enzymes effect the breakdown of structural proteins and are structurally related metalloproteases. These include human skin fibroblast collagenase, human skin fibroblast gelatinase, human sputum collagenase and gelatinase, and human stromelysin. These are zinc-containing metalloprotease enzymes, as are the angiotensin-converting enzymes and the enkephalinases. Collagenase, stromelysin and related enzymes are important in mediating the symptomatology of a number of diseases, including rheumatoid arthritis (Mullins, D. E., et al., Biochim Biophys Acta (1983) 695:117–214); osteoarthritis (Henderson, B., et al., Drugs of the Future (1990) 15:495–508); the metastasis of tumor cells (ibid. Broadhurst, M. J., et al., European Patent Application 276,436 (published 1987), Reich, R., et al., 48 *Cancer Res* 3307–3312 (1988); and various ulcerated conditions. Ulcerative conditions can result in the cornea as the result of alkali burns or as a result of infection by *Pseudomonas aeruginosa*, Acanthamoeba, Herpes simplex and vaccinia viruses.

Other conditions characterized by unwanted matrix metalloprotease activity include periodontal disease, epidermolysis bullosa and scleritis. In view of the involvement of matrix metalloproteases in a number of disease conditions, attempts have been made to prepare inhibitors to these enzymes. A number of such inhibitors are disclosed in the literature. Examples include U.S. Pat. No. 5,183,900, issued Feb. 2, 1993 to Galardy; U.S. Pat. No. 4,996,358, issued Feb. 26, 1991 to Handa, et al.; U.S. Pat. No. 4,771,038, issued Sep. 13, 1988 to Wolanin, et al.; U.S. Pat. No. 4,743,587, issued May 10, 1988 to Dickens, et at., European Patent Publication Number 575,844, published Dec. 29, 1993 by Broadhurst, et al.; International Patent Publication No. WO 93/09090, published May 13, 1993 by Isomura, et al.; World Publication 92/17460 Oct. 15, 1992 by Markwell et al.; and European Patent Publication Number 498,665, published Aug. 12, 1992 by Beckett, et al.

It is well known in the art that inhibitors of matrix metalloproteases are useful in treating diseases caused, at least in part, by breakdown of structural proteins. Though a variety of inhibitors have been prepared, there is a continuing need for potent matrix metalloprotease inhibitors useful in treating such diseases. Applicants have found that, surprisingly, the lactam-containing hydroxamic acids of the present invention are potent inhibitors of collagenase and/or stromelysin. The compounds of the present invention therefore may be useful for the treatment of conditions and diseases which are characterized by unwanted activity by the class of proteins which destroy structural proteins.

SUMMARY OF THE INVENTION

The invention provides compounds which are useful as inhibitors of matrix metalloproteases, and which are effective in treating conditions characterized by excess activity of these enzymes. In particular, the present invention relates to a compound having a structure according to Formula (I)

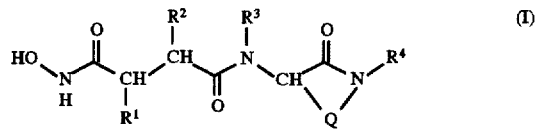

wherein (A) (1) (a) $R^1$ is hydrogen; alkyl; heteroalkyl; alkenyl; a heterocyclic ring; a carbocyclic ring; alkoxy; carbocycle-alkyl; heterocycle-alkyl; carbocycle-heteroalkyl; or heterocycle-heteroalkyl; and (b) $R^2$ is hydrogen; hydroxy; alkyl; alkenyl; alkynyl; heteroalkyl; a heterocyclic ring; a carbocyclic ring; carbocycle-alkyl; heterocycle-alkyl; or —OR, where R is alkyl, alkenyl, or carbocycle-alkyl; or (2) $R^1$ and $R^2$ together form a cyclo alkyl ring having from 3 to 8 ring atoms;

(B) $R^3$ is hydrogen; alkyl; or carbocycle-alkyl;

(C) $R^4$ is (1) alkyl;

(2) carbocycle-alkyl;

(3) —X—C(=Y)—Z—$R^5$ or —X—$CH_2$—Z—$R^5$, where (a) X is covalent bond or alkyl;

(b) Y is O, S, or NH;

(c) Z is O, S, or NH; and (d) $R^5$ is hydrogen; alkyl; alkenyl; carbocycle-alkyl; or aryl; or (4) —$SO_2$—$R^6$, where $R^6$ is alkyl, carbocylce-alkyl, heterocycle-alkyl, or aryl; and (D) Q is an alkyl chain, an alkenyl chain, a heteroalkyl chain, or a heteroalkenyl chain; wherein said chain has 2, 3, or 4 chain atoms and is unsubstituted or substituted with one or more alkyl moieties;

or a pharmaceutically-acceptable salt, or biohydrolyzable alkoxyamide, acyloxyamide, or imide thereof.

These compounds have the ability to inhibit at least one mammalian matrix metalloprotease. Accordingly, in other aspects, the invention is directed to pharmaceutical compositions containing the compounds of Formula (I), and to methods of treating diseases characterized by matrix metalloprotease activity using these compounds or the pharmaceutical compositions containing them.

Matrix metalloproteases at a particularly undesired location can be targeted by conjugating the compounds of the invention to a targeting ligand specific for a marker at that location such as an antibody or fragment thereof or a receptor ligand.

The invention is also directed to various other processes which take advantage of the unique properties of these compounds. Thus, in another aspect, the invention is directed to the compounds of Formula (I) conjugated to solid supports. These conjugates can be used as affinity reagents for the purification of a desired matrix metalloprotease.

In another aspect, the invention is directed to the compounds of Formula (I) conjugated to label. As the compounds of the invention bind to at least one matrix metalloprotease, the label can be used to detect the presence of relatively high levels of matrix metalloprotease in vivo or in vitro cell culture.

In addition, the compounds of Formula (I) can be conjugated to carriers which permit the use of these compounds in immunization protocols to prepare antibodies specifically immunoreactive with the compounds of the invention. These antibodies are then useful both in therapy and in monitoring the dosage of the inhibitors.

DETAILED DESCRIPTION

The compounds of the present invention are inhibitors of mammalian matrix metalloproteases. Preferably, the compounds are those of Formula (I) where the Q-containing heterocycle has one nitrogen atom. These compounds are the following

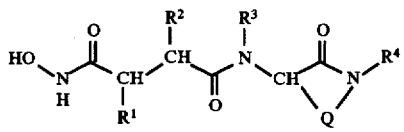

wherein (A) (1) (a) R$^1$ is hydrogen; alkyl; heteroalkyl; alkenyl; a heterocyclic ring; a carbocyclic ring; alkoxy; carbocycle-alkyl; heterocycle-alkyl; carbocycle-heteroalkyl; or heterocycle-heteroalkyl; and (b) R$^2$ is hydrogen; hydroxy; alkyl; alkenyl; alkynyl; heteroalkyl; a heterocyclic ring; a carbocyclic ring; carbocycle-alkyl; heterocycle-alkyl; or —OR, where R is alkyl, alkenyl, or carbocycle-alkyl; or (2) R$^1$ and R$^2$ together form a cycloalkyl ring having from 3 to 8 ring atoms;

(B) R$^3$ is hydrogen; alkyl; or carbocycle-alkyl;

(C) R$^4$ is (1) alkyl;

(2) carbocycle-alkyl;

(3) —X—C(=Y)—Z—R$^5$ or —X—CH$_2$—Z—R$^5$, where (a) X is covalent bond or alkyl;

(b) Y is O, S, or NH;

(c) Z is O, S, or NH; and (d) R$^5$ is hydrogen; alkyl; alkenyl; carbocycle-alkyl; or aryl; or (4) —SO$_2$—R$^6$, where R$^6$ is alkyl, carbocylce-alkyl, heterocycle-alkyl, or aryl; and (D) Q is —[—C(R$^7$)$_2$—]—$_n$, where (1) n is the integer 2, 3, or 4; and (2) each R$^7$ is independently hydrogen or alkyl so the Q-containing heterocycle is saturated; or the R$^7$ moiety on two adjacent carbon atoms is a covalent bond such that the Q-containing heterocycle in Formula (I) is unsaturated;

or a pharmaceutically-acceptable salt, or biohydrolyzable alkoxyamide, acyloxyamide, or imide thereof.

Definitions and Usage of Terms:

The following is a list of definitions for terms used herein.

"Acyl" or "carbonyl" is a radical formed by removal of the hydroxy from a carboxylic acid (i.e., R—C(=O)-). Preferred acyl groups include (for example) acetyl, formyl, and propionyl.

"Acyloxy" is an oxygen radical having an acyl substituent (i.e., —O—acyl); for example, —O—C(=O)—alkyl.

"Acylamino" is an amino radical having an acyl substituent (i.e., —N—acyl); for example, —NH—C(=O)-alkyl.

"Alkoxyacyl" is an acyl radical (—C(=O)-) having an alkoxy subtituent (i.e., —O—R), for example, —C(=O)—O—alkyl.

"Alkenyl" is an unsubstituted or substituted hydrocarbon chain radical having 2, 3, 4, 5, 6, 7, 8, 9, 10, 11, 12, 13, 14 or 15 carbon atoms; preferably from 2 to 10 carbon atoms; more preferably from 2 to 8; except where indicated. Alkenyl substituents have at least one olefinic double bond (including, for example, vinyl, allyl and butenyl).

"Alkynyl" is an unsubstituted or substituted hydrocarbon chain radical having 2, 3, 4, 5, 6, 7, 8, 9, 10, 11, 12, 13, 14 or 15 carbon atoms; preferably from 2 to 10 carbon atoms; more preferably from 2 to 8; except where indicated. The chain has at least one carbon-carbon triple bond.

"Alkoxy" is an oxygen radical having a hydrocarbon chain substituent, where the hydrocarbon chain is an alkyl or alkenyl (i.e., —O—alkyl or —O—alkenyl). Preferred alkoxy groups include (for example) methoxy, ethoxy, propoxy and allyloxy.

"Alkoxyalkyl" is an unsubstituted or substituted alkyl moiety substituted with an alkoxy moiety (i.e., —alkyl—O—alkyl). Preferred is where the alkyl has 1, 2, 3, 4, 5 or 6 carbon atoms (more preferably 1 to 3 carbon atoms), and the alkyoxy has 1, 2, 3, 4, 5 or 6 carbon atoms (more preferably 1 to 3 carbon atoms).

"Alkyl" is an unsubstituted or substituted saturated hydrocarbon chain radical having 1, 2, 3, 4, 5, 6, 7, 8, 9, 10, 11, 12, 13, 14 or 15 carbon atoms; preferably from 1 to 10 carbon atoms; more preferably 1 to 4; except where indicated. Preferred alkyl groups include (for example) substituted or unsubstituted methyl, ethyl, propyl, isopropyl, and butyl.

"Alkylamino" is an amino radical having one (secondary amine) or two (tertiary amine) alkyl substituents (i.e., —N—alkyl). For example, methylamine (—NHCH$_3$), dimethylamine (—N(CH$_3$)$_2$), methylethylamine (—N(CH$_3$)CH$_2$CH$_3$).

"Aminoacyl" is acyl radical having an amino substituent (i.e., —C(=O)—N); for example, —C(=O)—NH$_2$. The amino group of the aminoacyl moiety may be unsubstituted (i.e., primary amine) or may be substituted with one (secondary amine) or two (i.e., tertiary amine) alkyl groups.

"Aryl" is an aromatic carbocyclic ring radical. Preferred aryl groups include (for example) phenyl, tolyl, xylyl, cumenyl and naphthyl.

"Arylalkyl" is an alkyl radical substituted with an aryl group. Preferred arylalkyl groups include benzyl, phenylethyl, and phenylpropyl.

"Arylalkylamino" is an amine radical substituted with an arylalkyl group (e.g., —NH—benzyl).

"Arylamino" is an amine radical substituted with an aryl group (i.e., —NH—aryl).

"Aryloxy" is an oxygen radical having an aryl substituent (i.e., —O—aryl).

"Carbocyclic ring" is an unsubstituted or substituted, saturated, unsaturated or aromatic, hydrocarbon ring radical. Carbocyclic rings are monocyclic or are fused, bridged or spiro polycyclic ring systems. Monocyclic carbocyclic rings generally contain 3, 4, 5, 6, 7, 8 or 9 atoms, preferably 3 to 6 atoms. Polycyclic carbocyclic rings contain 7, 8, 9, 10, 11, 12, 13, 14, 15, 16 or 17 atoms, preferably from 7 to 13 atoms.

"Carbocycle-alkyl" is an unsubstituted or substituted alkyl radical substituted with a carbocyclic ring. Unless otherwise specified, the carbocyclic ring is preferably an aryl or cycloalkyl; more preferably an aryl. Preferred carbocycle-alkyl groups include benzyl, phenylethyl and phenylpropyl.

"Carbocycle-heteroalkyl" is an unsubstituted or substituted heteroalkyl radical substituted with a carbocyclic ring. Unless otherwise specified, the carbocyclic ring is preferably an aryl or cycloalkyl; more preferably an aryl. The heteroalkyl is preferably 2-oxa-propyl, 2-oxa-ethyl, 2-thia-propyl, or 2-thia-ethyl.

"Carboxyalkyl" is an unsubstituted or substituted alkyl radical substituted with with a carboxy (—C(=O)OH) moiety. For example, —CH$_2$—C(=O)OH.

"Cycloalkyl" is a saturated carbocyclic ring radical. Preferred cycloalkyl groups include (for example) cyclopropyl, cyclobutyl and cyclohexyl.

"Cycloheteroalkyl" is a saturated heterocyclic ring. Preferred cycloheteroalkyl groups include (for example) morpholine, piperadine, and piperazine.

"Fused rings" are rings that are superimposed together such that they share two ring atoms. A given ring may be fused to more than one other ring.

"Heterocycle-alkyl" is an alkyl radical substituted with a heterocyclic ring. The heterocyclic ring is preferably an heteroaryl or cycloheteroalkyl; more preferably an heteroaryl.

"Heterocycle-heteroalkyl" is an unsubstituted or substituted heteroalkyl radical substituted with a heterocyclic ring. The heterocyclic ring is preferably an aryl or cycloheteroalkyl; more preferably an aryl.

"Heteroatom" is a nitrogen, sulfur or oxygen atom. Groups containing one or more heteroatoms may contain different heteroatoms.

"Heteroalkenyl" is an unsubstituted or substituted unsaturated chain radical having 3, 4, 5, 6, 7 or 8 members comprising carbon atoms and one or two heteroatoms. The chain has at least one carbon-carbon double bond.

"Heteroalkyl" is an unsubstituted or substituted saturated chain radical having 2, 3, 4, 5, 6, 7 or 8 comprising carbon atoms and one or two heteroatoms.

"Heterocyclic ring" is an unsubstituted or substituted, saturated, unsaturated or aromatic ring radical comprised of carbon atoms and one or more heteroatoms in the ring. Heterocyclic rings are monocyclic or are fused, bridged or spiro polycyclic ring systems. Monocyclic heterocyclic rings contain 3, 4, 5, 6, 7, 8 or 9 atoms, preferably 4 to 7 atoms. Polycyclic rings contain 7, 8, 9, 10, 11, 12, 13, 14, 15, 16 or 17 atoms, preferably from 7 to 13 atoms.

"Heteroaryl" is an aromatic heterocyclic ring radical. Preferred heteroaryl groups include (for example) thienyl, furyl, pyrrolyl, pyridinyl, pyrazinyl, thiazolyl, pyrimidinyl, quinolinyl, and tetrazolyl.

"Halo", "halogen", or "halide" is a chloro, bromo, fluoro or iodo atom radical. Chloro and fluoro are preferred halides.

Also, as referred to herein, a "lower" hydrocarbon moiety (e.g., "lower" alkyl) is a hydrocarbon chain comprised of 1, 2, 3, 4, 5 or 6, preferably from 1 to 4, carbon atoms.

A "pharmaceutically-acceptable salt" is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987 (incorporated by reference herein). Preferred cationic salts include the alkali metal salts (such as sodium and potassium), and alkaline earth metal salts (such as magnesium and calcium). Preferred anionic salts include the halides (such as chloride salts).

"Biohydrolyzable alkoxyamide" and "Biohydrolyzable acyloxyamide" are amides of a hydroxamic acid that do not essentially interfere with the inhibitory activity of the compound, or that are readily converted in vivo by a human or lower animal subject to yield an active hydroxamic acid. A biohydrolyzable alkoxyamide derivative of the Formula (I) compounds is represented by the following:

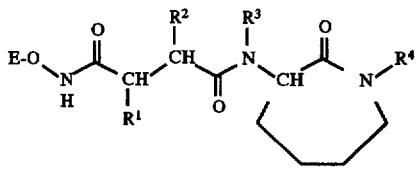

where E is an alkyl moieity. A biohydrolyzable acyloxyamide derivative of the Formula (I) compounds is where E is an acyl moiety (e.g. R—C(=O)-).

A "biohydrolyzable hydroxy imide" is an imide of a Formula (I) compound that does not interfere with the metalloprotease inhibitory activity of these compounds, or that is readily converted in vivo by a human or lower animal subject to yield an active Formula (I) compound. Such hydroxy imides include those that do not interfere with the biological activity of the Formula (I) compounds. These imides have a structure according to the following:

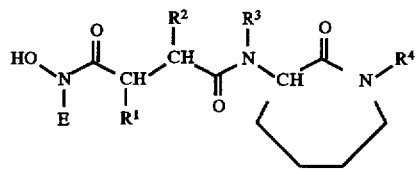

where E is an acyl moiety (e.g., —C(=O)—R).

A "solvate" is a complex formed by the combination of a solute (e.g., a hydroxamic acid) and a solvent (e.g., water). See J. Honig et al., The Van Nostrand Chemist's Dictionary, p. 650 (1953). Pharmaceutically-acceptable solvents used according to this invention include those that do not interfere with the biological activity of the hydroxamic acid (e.g., water, ethanol, acetic acid, N,N-dimethylformamide).

The illustration of specific protected forms and other derivatives of the Formula (I) compounds is not intended to be limiting. The application of other useful protecting groups, salt forms, etc. is within the ability of the skilled artisan.

As defined above and as used herein, substituent groups may themselves be substituted. Such substitution may be with one or more substituents. Such substituents include those listed in C. Hansch and A. Leo, Substituent Constants for Correlation Analysis in Chemistry and Biology (1979), incorporated by reference herein. Preferred substituents include (for example) alkyl, alkenyl, alkoxy, hydroxy, oxo, nitro, amino, aminoalkyl (e.g., aminomethyl, etc.), cyano, halo, carboxy, alkoxyaceyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

As used herein, "mammalian matrix metalloprotease" means any metal-containing enzyme found in mammalian sources which is capable of catalyzing the breakdown of collagen, gelatin or proteoglycan under suitable assay conditions. Appropriate assay conditions can be found, for example, in U.S. Pat. No. 4,743,587, which references the procedure of Cawston, et al., Anal Biochem (1979) 99:340–345, use of a synthetic substrate is described by Weingarten, H., et al., Biochem Biophy Res Comm (1984) 139:1184–1187. Any standard method for analyzing the breakdown of these structural proteins can, of course, be used. The matrix metalloprotease enzymes referred to herein are all zinc-containing proteases which are similar in structure to, for example, human stromelysin or skin fibroblast collagenase. The ability of candidate compounds to inhibit matrix metalloprotease activity can, of course, be tested in the assays described above. Isolated matrix metalloprotease enzymes can be used to confirm the inhibiting activity of the invention compounds, or crude extracts which contain the range of enzymes capable of tissue breakdown can be used.

Compounds:

Referring to Formula (I), the $R^1$ substituent group is selected from hydrogen; alkyl; heteroalkyl; alkenyl; a heterocyclic ring; a carbocyclic ring; alkoxy; carbocycle-alkyl; heterocycle-alkyl; carbocycle-heteroalkyl; and heterocycle-heteroalkyl. Preferred is where $R^1$ is hydrogen; alkyl; alkenyl; a heterocyclic ring; alkoxy; carbocycle-alkyl; or aminoalkyl. More preferred is where $R^1$ is hydrogen; $C_1$-$C_8$ alkyl; aminoalkyl; or benzyl. Most preferred is where $R^1$ is hydrogen, methyl, ethyl, or propyl.

$R^2$ is selected from hydrogen; hydroxy; alkyl; alkenyl; alkynyl; heteroalkyl; a heterocyclic ring; a carbocyclic ring; carbocycle-alkyl; heterocycle-alkyl; and —OR, where R is alkyl, alkenyl, or carbocycle-alkyl. Preferred is where $R^2$ is hydrogen; alkyl; or aminoalkyl. More preferred is where $R^2$ is hydrogen or $C_1$-$C_8$ alkyl. Particularly preferred is where $R^2$ is n-octyl, n-pentyl or 2-methylpropyl.

In the alternative, $R^1$ and $R^2$ can together form a cycloalkyl ring having from 3 to 8 ring atoms; preferably 5 to 7 ring atoms; more preferably 6 atoms. Preferred is where $R^1$ and $R^2$ do not combine to form a ring.

$R^3$ is selected from hydrogen; alkyl; and carbocycle-alkyl (more preferably $C_1$-$C_2$ alkyl). Preferred is where $R^3$ is hydrogen.

$R^4$ is selected from alkyl; carbocycle-alkyl; alkoxyalkyl; —X—C(=Y)—Z—$R^5$ or —X—CH$_2$—Z—$R^5$, where (a) X is covalent bond or alkyl; (b) Y is O, S, or NH; (c) Z is O, S, or NH; $R^5$ is hydrogen; alkyl, alkenyl, carbocycle-alkyl, or aryl.

When $R^4$ is alkyl, preferred is $C_1$-$C_8$ alkyl.

When $R^4$ is —X—C(=Y)—Z—$R^5$, X is preferably $C_1$-$C_3$ alkyl (more preferably $C_1$-$C_2$ alkyl), Y is preferably O, and Z is preferably NH or O. When Y and Z are both O, $R^5$ is preferably alkyl (preferably methyl or ethyl; most preferably methyl) or carbocycle-alkyl (preferably benzyl); most preferably alkyl. When Y is O and Z is NH, $R^5$ is preferably alkyl or carbocycle-alkyl; more preferably methyl, ethyl, butyl, or benzyl.

When $R^4$ is —X—CH$_2$—Z—$R_5$, X is preferably $C_1$-$C_3$ alkyl, Z is preferably O or S, and $R^5$ is preferably alkyl or carbocycle-alkyl (more preferably alkyl). Particularly preferred is where X is $C_1$, Z is O and $R^5$ is $C_1$-$C_3$ alkyl.

When $R^4$ is —SO$_2R^6$, $R^6$ is alkyl, carbocycle-alkyl, heterocycle-alkyl, or aryl; preferably aryl (preferably phenyl; most preferably 4-methylphenyl).

As indicated above, particularly preferred compounds of the present invention are those where the Q-containing heterocycle has only one ring nitrogen atom. That is, where Q is -[—C(R$^7$)$_2$-]$_n$, where n is the integer 2, 3, or 4 (more preferably 3 or 4). Particurlary preferred is where n is 4, such that the Q-containing heterocycle has 7 ring atoms. Each $R^7$ is independently hydrogen or alkyl; or the $R^7$ moiety on two adjacent carbon atoms is a covalent bond such that the Q-containing heterocycle in Formula (I) is unsaturated. Preferred compounds are those where the Q-containing heterocycle is saturated; most preferably where each $R^7$ is hydrogen.

The following illustrates compounds where the Q-containing heterocycle is unsaturated:

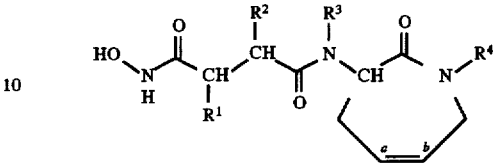

In this structure, the heterocycle has seven members (i.e., n=4). Referring to Formula (I), carbon atoms a and b each represent a —C($R^7$)$_2$- moiety where one $R^7$ is hydrogen and the other is a covalent bond, such that a double bond exists between atoms a and b.

Two groups of adjacent carbon atoms may have $R^7$ moieties that are covalent bonds, such that the lactam ring has two points of unsaturation (i.e., two double bonds). The following illustrates such rings where the Q-containing heterocylce has two points of unsaturation:

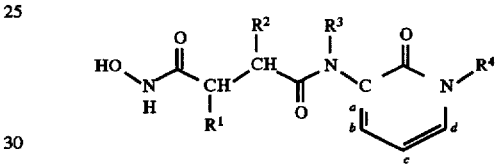

In this structure, the heterocycle has six members (i.e., n=3). Referring to Formula (I), carbon atoms a and b each represent a —C($R^7$)$_2$— moiety where one $R^7$ is hydrogen and the other is a covalent bond, such that a double bond exists between atoms a and b. In addition, c and d each represents a —C($R^7$)$_2$— moiety where one $R^7$ is hydrogen and the other is a covalent bond, such that a double bond exists between atoms c and d.

The following table lists representative preferred compounds within the scope of the invention. The table is not intended to be an exhaustive list of the compounds within the scope of the invention. Referring to Formula (I), Q is (—CH$_2$—)$_n$, n is 4, and $R^3$ is hydrogen in each instance.

| Cmp. | $R^1$ | $R^2$ | $R^4$ |
|---|---|---|---|
| 1 | hydrogen | 2-methylpropyl | —CH$_1$—C(=O)—O—CH$_3$ |
| 2 | hydrogen | 2-methylpropyl | —CH$_2$—C(=O)—NH—CH$_3$ |
| 3 | hydrogen | 2-methylpropyl | —CH$_2$—C(=O)—O—C(CH$_3$)$_3$ |
| 4 | hydrogen | 2-methylpropyl | —CH$_2$-phenyl |
| 5 | hydrogen | 2-methylpropyl | —CH$_2$—C(=O)—O—CH$_2$-phenyl |
| 6 | hydrogen | 2-methylpropyl | —CH$_2$—C(=O)—NH—CH$_2$-phenyl |
| 7 | hydrogen | 2-methylpropyl | —CH$_2$—C(=O)—O—CH$_3$ |
| 8 | hydrogen | —(CH$_2$)$_4$CH$_3$ | —CH$_2$—C(=O)—NH—(CH$_2$)$_3$—CH$_3$ |
| 9 | hydrogen | —(CH$_2$)$_7$CH$_3$ | —CH$_2$—C(=O)—O—CH$_3$ |
| 10 | hydrogen | —(CH$_2$)$_7$CH$_3$ | —O$_2$-phenyl |
| 11 | hydrogen | —(CH$_2$)$_7$CH$_3$ | —CH$_2$—CH$_2$—O—CH$_3$ |
| 12 | hydrogen | —(CH$_2$)$_7$CH$_3$ | —(CH$_2$)$_3$CH$_3$ |
| 13 | CH$_3$ (S form) | 2-methylpropyl | —CH$_2$—C(=O)—O—CH$_3$ |
| 14 | CH$_3$ (R form) | 2-methylpropyl | —CH$_2$—C(=O)—O—CH$_3$ |
| 15 | CH$_3$CH$_2$CH$_2$— | 2-methylpropyl | —CH$_2$—C(=O)—O—CH$_3$ |
| 16 | —(CH$_2$)$_2$—CH$_2$OH (S form) | 2-methylpropyl | —CH$_2$—C(=O)—O—CH$_3$ |
| 17 | CH$_3$ (S form) | —(CH$_2$7CH$_3$ | —CH$_2$—C(=O)—O—CH$_3$ |
| 18 | CH$_3$ (R form) | —(CH$_2$7CH$_3$ | —CH$_2$—C(=O)—O—CH$_3$ |
| 19 | CH$_3$ (S form) | —(CH$_2$7CH$_3$ | —CH$_2$—CH$_2$—O—CH$_3$ |
| 20 | CH$_3$ (R form) | —(CH$_2$7CH$_3$ | —CH$_2$—CH$_2$—O—CH$_3$ |

General Schemes for Compound Preparation:

The hydroxamic compounds of Formula (I) can be prepared using a variety of procedures. General schemes include the following. (Representative examples are described for making specific compounds hereinbelow.)

a. General Scheme 1:

Commercially available Caprolactam (A) is protected to give (B), followed by alkylation of the amydic nitrogen under appropriate conditions to give (C). The derivatized lactam (C) is deprotected under acidic conditions to give the amine salt (D) which is then used for coupling to various succinates as described in Scheme 2 and 3.

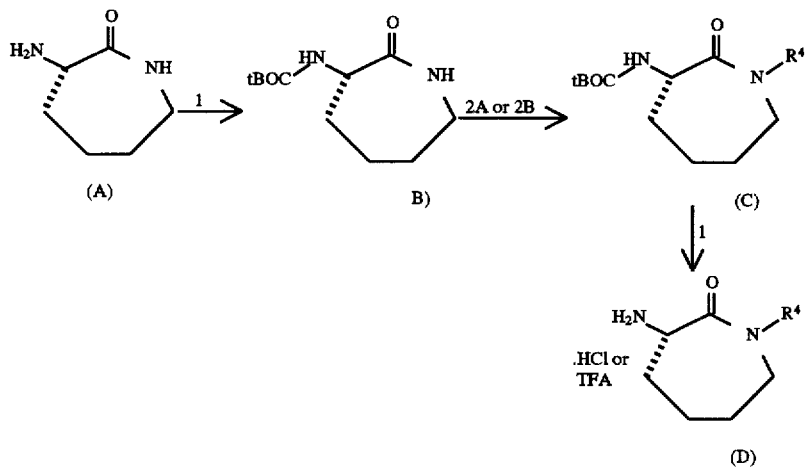

1) (BOC)$_2$O, DMSO; 2A) LiN(TMS)$_2$; R$^4$—X, THF;
2B) t-BuOK, R$^4$—X, DMF; 3) TFA/CH$_2$Cl$_2$ or HCl/Et$_2$O

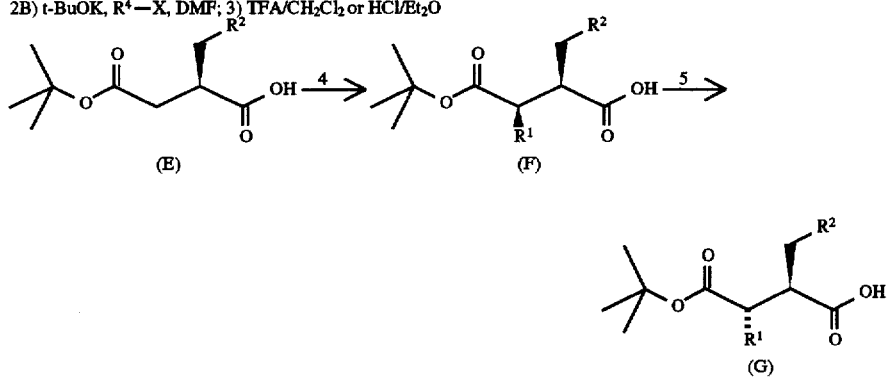

4) LiN(TMS)$_2$, THF, R$^1$—X; 5) LDA, THF

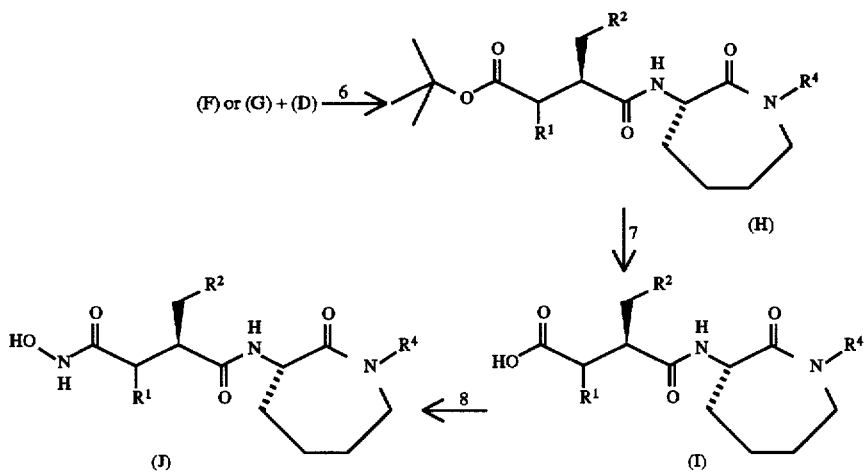

6) EDAC, HOBT, NMM, DMF, 0deg. C; 7) TFA, CH$_2$Cl$_2$;
8A-i) EDAC, HOBT, NMM, DMF, BnONH$_2$.HCl, 0 deg. C; ii) H$_2$/Pd—C, EtOH;
8B-i) CH$_2$N$_2$; ii) NH$_2$OH.HCl/KOH, MeOH The various alkyl succinates (E) are synthesized following Evan's chiral alkylation method (D. A. Evans, et al., *Org. Synth.* Vol. 86, p 83 (1990), incorporated herein by reference). The dianion generated by treating (E) with a hindered base is alkylated to give syn-disubstituted succinates (F) which on further treatment with LDA gives the desired anti-diastereomer (G) in reasonable yield (H. L Crimmin, et al., *Synlett*, 137–138 (1993)).

The acid (F) or (G) and the amine salt (D) are coupled under a mild condition to give the amide (H) (depicted without specifying stereochemistry), which on deprotection under acidic conditions gives the corresponding acid (I). A final transformation is carried out to convert the purified acid to the desired inhibitor (J).

b. General Scheme 2:

c. General Scheme 3:

The compounds of the present invention having a lactam ring with 5 or 6 members can be prepared as follows.

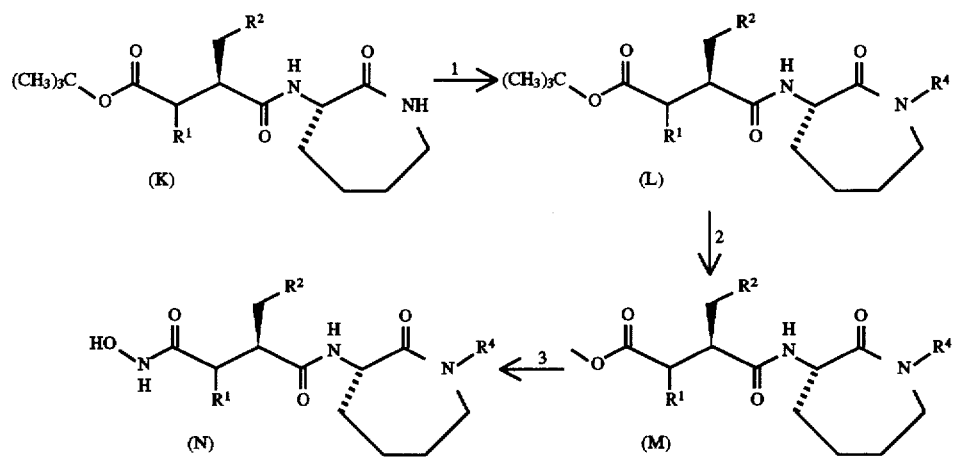

A direct alkylation method can also be utilized to synthesize the final inhibitors. For example, the treatment of

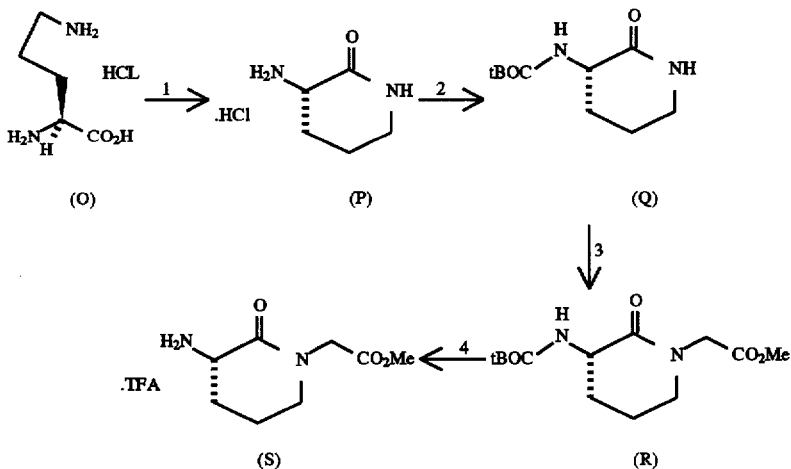

intermediate (K) (prepared by reacting Compound A with Compound F or G according to Scheme 1) with a hindered base at low temperature followed by a quench of the anion with an alkylating agent gives (L) which on deprotection under acidic conditions and re-esterification provides (M) in good yield. A direct treatment of this ester with freshly-generated hydroxylamine then produces the final inhibitor (N).

For example, L-ornithine hydrochloride (O) on heating under reflux provides the six-membered lactam (P) which on further protection with BOC-anhydride produces the desired amide (Q) in reasonable yield. This intermediate can then be carried on to the final product (S) following a method as described in the preceding schemes. For 5-membered lactams, L-ornithine hydrochloride (Compound (O)) is replaced by (COOH)CH(NH$_2$)CH$_2$CH$_2$NH$_2$ as the starting material.

d. General Scheme 4:

Modifications of the ring system described in General Scheme 3 can also be made via the following a method, to provide unsaturation in the Q-containing ring.

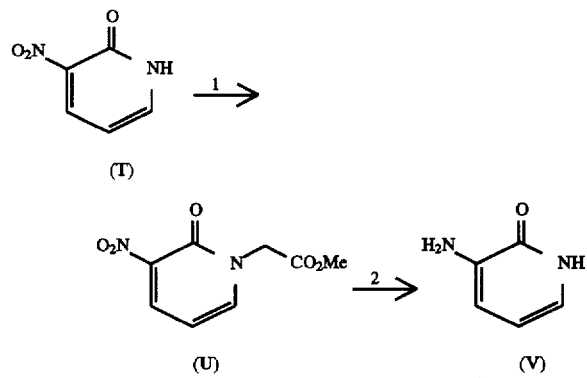

Here, a properly-substituted pyrimidone (T) is N-alkylated under appropriate conditions to give (U). The resultant product, in this case the nitro-pyrimidone (U), is reduced to provide the desired amine (V). This intermediate is coupled to the succinate (F) or (G) described in Scheme 1 (see Scheme 1 for the synthesis of final products). A variety of ring systems can be generated in a similar fashion.

Compositions:

The compositions of the invention comprise:

(a) a safe and effective amount of a compound of Formula (I); and (b) a pharmaceutically-acceptable carrier.

As discussed above, numerous diseases are known to be mediated by excess or undesired matrix-destroying metalloprotease activity. These include tumor metastasis, osteoarthritis, rheumatoid arthritis, skin inflammation, ulcerations, particularly of the cornea, reaction to infection, periodontitis and the like. Thus, the compounds of the invention are useful in therapy with regard to conditions involving this unwanted activity.

The invention compounds can therefore be formulated into pharmaceutical compositions for use in treatment or prophylaxis of these conditions. Standard pharmaceutical formulation techniques are used, such as those disclosed in Remington's Pharmaceutical Sciences, Mack Publishing Company, Easton, Pa., latest edition.

A "safe and effective amount" of a Formula (I) compound is an amount that is effective, to inhibit matrix metalloproteases at the site(s) of activity, in a human or lower animal subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the Formula (I) compound therein, and the dosage regimen desired for the composition.

The compositions of this invention are preferably provided in unit dosage form. As used herein, a "unit dosage form" is a composition of this invention containing an amount of a Formula (I) compound that is suitable for administration to a human or lower animal subject, in a single dose, according to good medical practice. These compositions preferably contain from about 5 mg (milligrams) to about 1000 mg, more preferably from about 10 mg to about 500 mg, more preferably from about 10 mg to about 300 mg, of a Formula (I) compound.

The compositions of this invention may be in any of a variety of forms, suitable (for example) for oral, rectal, topical or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the inhibitory activity of the Formula (I) compound. The amount of carrier employed in conjunction with the Formula (I) compound is sufficient to provide a practical quantity of material for administration per unit dose of the Formula (I) compound. Techniques and compositions for making dosage forms useful in the methods of this invention are described in the following references, all incorporated by reference herein: *Modern Pharmaceutics*, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

Various oral dosage forms can be used, including such solid forms as tablets, capsules, granules and bulk powders. These oral forms comprise a safe and effective amount, usually at least about 5%, and preferably from about 25% to about 50%, of the Formula (I) compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The compositions of this invention can also be administered topically to a subject, i.e., by the direct laying on or spreading of the composition on the epidermal or epithelial tissue of the subject. Such compositions include, for example, lotions, creams, solutions, gels and solids. These topical compositions preferably comprise a safe and effective amount, usually at least about 0.1%, and preferably from about 1% to about 5%, of the Formula (I) compound. Suitable carriers for topical administration preferably remain in place on the skin as a continuous film, and resist being removed by perspiration or immersion in water. Generally, the carrier is organic in nature and capable of having dispersed or dissolved therein the Formula (I) compound. The carrier may include pharmaceutically-acceptable emollients, emulsifiers, thickening agents, and solvents.

Methods of Administration:

This invention also provides methods of treating or preventing disorders associated with excess or undesired matrix metalloprotease activity in a human or other animal subject, by administering a safe and effective amount of a Formula (I) compound to said subject. As used herein, a "disorder associated with excess or undesired matrix metalloprotease activity" is any disorder characterized by degradation of matrix proteins. The methods of the invention are useful in treating disorders such as (for example) osteoarthritis, periodontitis, corneal ulceration, tumor invasion, and rheumatoid arthritis.

The Formula (I) compounds and compositions of this invention can be administered topically or systemically. Systemic application includes any method of introducing Formula (I) compound into the tissues of the body, e.g., intra-articular (especially in treatment of rheumatoid arthritis), intrathecal, epidural, intramuscular, transdermal, intravenous, intraperitoneal, subcutaneous, sublingual, rectal, and oral administration. The Formula (I) compounds of the present invention are preferably administered orally.

The specific dosage of inhibitor to be administered, as well as the duration of treatment, are mutually dependent. The dosage and treatment regimen will also depend upon such factors as the specific Formula (I) compound used, the treatment indication, the ability of the Formula (I) compound to reach minimum inhibitory concentrations at the site of the matrix metalloprotease to be inhibited, the personal attributes of the subject (such as weight), compliance with the treatment regimen, and the presence and severity of any side effects of the treatment.

Typically, for a human adult (weighing approximately 70 kilograms), from about 5 mg to about 3000 mg, more preferably from about 5 mg to about 1000 mg, more preferably from about 10 mg to about 100 mg, of Formula (I) compound are administered per day. It is understood that these dosage ranges are by way of example only, and that daily administration can be adjusted depending on the factors listed above.

A preferred method of administration for treatment of rheumatoid arthritis is oral or parenterally via intra-articular injection. As is known and practiced in the art, all formulations for parenteral administration must be sterile. For mammals, especially humans, (assuming an approximate body weight of 70 kilograms) individual doses of from about 10 mg to about 1000 mg are preferred.

A preferred method of systemic administration is oral. Individual doses of from about 10 mg to about 1000 mg, preferably from about 10 mg to about 300 mg are preferred.

Topical administration can be used to deliver the Formula (I) compound systemically, or to treat a subject locally. The amounts of Formula (I) compound to be topically administered depends upon such factors as skin sensitivity, type and location of the tissue to be treated, the composition and carrier (if any) to be administered, the particular Formula (I) compound to be administered, as well as the particular disorder to be treated and the extent to which systemic (as distinguwashed from local) effects are desired.

The inhibitors of the invention can be targeted to specific locations where the matrix metalloprotease is accumulated by using targeting ligands. For example, to focus the inhibitors to matrix metalloprotease contained in a tumor, the inhibitor is conjugated to an antibody or fragment thereof which is immunoreactive with a tumor marker as is generally understood in the preparation of immunotoxins in general. The targeting ligand can also be a ligand suitable for a receptor which is present on the tumor. Any targeting ligand which specifically reacts with a marker for the intended target tissue can be used. Methods for coupling the invention compound to the targeting ligand are well known and are similar to those described below for coupling to carrier. The conjugates are formulated and administered as described above.

For localized conditions, topical administration is preferred. For example, to treat ulcerated cornea, direct application to the affected eye may employ a formulation as eyedrops or aerosol. For corneal treatment, the compounds of the invention can also be formulated as gels or ointments, or can be incorporated into collagen or a hydrophilic polymer shield. The materials can also be inserted as a contact lens or reservoir or as a subconjunctival formulation. For treatment of skin inflammation, the compound is applied locally and topically, in a gel, paste, salve or ointment. The mode of treatment thus reflects the nature of the condition and suitable formulations for any selected route are available in the art.

In all of the foregoing, of course, the compounds of the invention can be administered alone or as mixtures, and the compositions may further include additional drugs or excipients as appropriate for the indication.

Some of the compounds of the invention also inhibit bacterial metalloproteases although generally at a lower level than that exhibited with respect to mammalian metalloproteases. Some bacterial metalloproteases seem to be less dependent on the stereochemistry of the inhibitor, whereas substantial differences are found between diastereomers in their ability to inactivate the mammalian proteases. Thus, this pattern of activity can be used to distinguish between the mammalian and bacterial enzymes.

Preparation and Use of Antibodies:

The invention compounds can also be utilized in immunization protocols to obtain antisera immunospecific for the invention compounds. As the invention compounds are relatively small, they are advantageously coupled to antigenically neutral carriers such as the conventionally used keyhole limpet hemocyanin (KLH) or serum albumin carriers. For those invention compounds having a carboxyl functionality, coupling to carrier can be done by methods generally known in the art. For example, the carboxyl residue can be reduced to an aldehyde and coupled to carrier through reaction with sidechain amino groups in protein-based carriers, optionally followed by reduction of imino linkage formed. The carboxyl residue can also be reacted with sidechain amino groups using condensing agents such as dicyclohexyl carbodiimide or other carbodiimide dehydrating agents.

Linker compounds can also be used to effect the coupling; both homobifunctional and heterobifunctional linkers are available from Pierce Chemical Company, Rockford, Ill. The resulting immunogenic complex can then be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures, now standard in the art, employing the invention compounds as antigens.

The antisera obtained can be used directly or monoclonal antibodies may be obtained by harvesting the peripheral blood lymphocytes or the spleen of the immunized animal and immortalizing the antibody-producing cells, followed by identifying the suitable antibody producers using standard immunoassay techniques.

The polyclonal or monoclonal preparations are then useful in monitoring therapy or prophylaxis regimens involving the compounds of the invention. Suitable samples such as those derived from blood, serum, urine, or saliva can be tested for the presence of the administered inhibitor at various times during the treatment protocol using standard immunoassay techniques which employ the antibody preparations of the invention.

The invention compounds can also be coupled to labels such as scintigraphic labels, e.g., technetium 99 or I-131, using standard coupling methods. The labeled compounds are administered to subjects to determine the locations of excess amounts of one or more matrix metalloproteases in vivo. The ability of the inhibitors to selectively bind matrix metalloprotease is thus taken advantage of to map the distribution of these enzymes in situ. The techniques can also be employed in histological procedures and the labeled invention compounds can be used in competitive immunoassays.

The following non-limiting examples illustrate the compounds, compositions, and uses of the present invention.

EXAMPLE 1

Synthesis of (2R)-Isobutyl-3-(N-hydroxycarboxamido)-propanoic acid amide of 1N-(carbomethoxymethyl)-caprolactam-(3S)-amine (1)

(26). The caprolactam 25 (914 mg, 2.69 mmole) is taken in 10 mL THF and cooled to −78° C. under argon. To this is added 1M lithium bis(trimethylsilyl)amide (2.69 mL, 2.69 mmole) and the reaction stirred for 5 min. Methyl bromoacetate (256 μL, 2.69 mmole) is added and stirred for 2 hr. The reaction is then partitioned between water and EtOAc. The organic layer is then washed with 1N HCl, NaHCO$_3$, and brine, dried over MgSO$_4$, filtered and evaporated to give crude material which is then chromatographed over flash silica with hexanes:EtOAc (1:4) to give 26.

(2R)-Isobutyl-3-carboxypropanoic acid amide of N-(carbomethoxymethyl)-caprolactam-(3S)-amine (27). Trifluoroacetic acid (3 mL) is added via syringe to a solution of tert-butyl ester 26 (380 mg, 0.922 mmole) in 3 mL CH$_2$Cl$_2$ under argon and the resulting mixture is stirred for 2 hr at room temperature. The material is then concentrated under vacuum to give 27 which is carried forward without purification.

(2R)-Isobutyl-3-(O-benzyl-N-hydroxycarboxamido)-propanoic acid amide of 1N-(carbomethoxymethyl)-caprolactam-(3S)-amine (28). A mixture of acid 27 (345 mg, 0.863 mmole), O-benzyl hydroxylamine hydrochloride (166 mg, 1.035 mmole) and HOBT (397 mg, 2.59 mmole) in 5

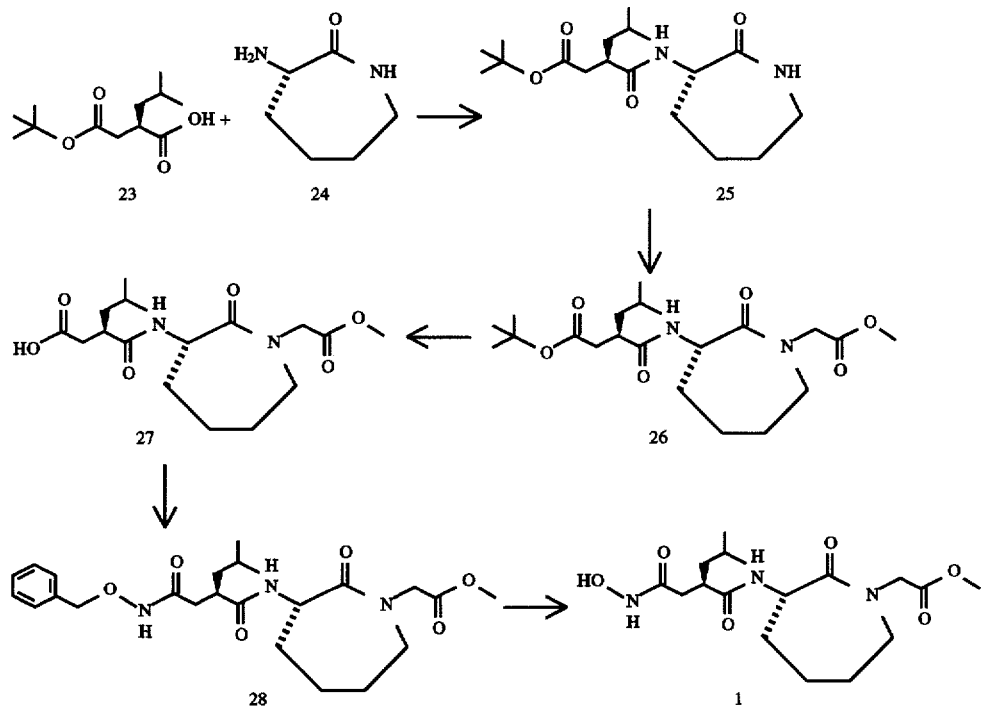

(2R)-Isobutyl-3-carbo-tert-butoxypropionic acid amide of caprolactam-(3S)-amine (25). A mixture of acid 23 (2.0 g, 8.70 mmole), caprolactam-[3S]-amine 24 (1.23 g, 9.57 mmole) and 1-Hydroxybenzotriazole hydrate ("HOBT") (4.0 g, 26.1 mmole) in 40 mL of DMF and 1.6 mL of N-Methylmorpholine ("NMM") is charged with 1-Ethyl-3-(3-dimethylaminopropyl)carbodiimide ("EDAC") (2.0 g, 10.44 mmole) and the reaction is stirred for 15 hr at room temperature. The reaction is then partitioned between water and ethyl acetate ("EtOAc"). The organic layer is then washed with 1N HCl, NaHCO$_3$, and brine, dried over MgSO$_4$, filtered, evaporated and chromatographed over flash silica with EtOAc to give 25.

(2R)-Isobutyl-3-carbo-tert-butoxypropanoic acid amide of 1N-(carbomethoxy-methyl)-caprolactam-(3S)-amine mL of N,N-Dimethylformamide ("DMF") and 260 μL of NMM is charged with EDAC (199 mg, 1.035 mmole) and the reaction is stirred for 15 hr at room temperature. The reaction is then partitioned between water and EtOAc. The organic layer is then washed with 1N HCl, NaHCO$_3$, and brine, dried over MgSO$_4$, filtered and evaporated to give crude material which is then chromatographed over flash silica with EtOAc to give the title compound 28.

(2R)-Isobutyl-3-(N-hydroxycarboxamido)-propanoic acid amide of 1N-(carbomethoxy-methyl)-caprolactam-(3S)-amine (1). The benzyl hydroxamic acid 28 (325 mg, 0.705 mmole) is taken in 6 mL EtOH and the mixture is charged with 10% palladium on carbon (60 mg) and stirred under one atmosphere of hydrogen for 45 min. The mixture is then filtered through celite and concentrated to give 240 mg of crude material which is then chromatographed over flash silica with EtOAc:formic acid (98:2) and then recrystallized from hexanes:EtOAc (2:1) to give the pure desired hydroxamic acid 1.

EXAMPLE 2

Synthesis of (2R)-Isobutyl-3-(N-hydroxycarboxamido)-propionic acid amide of 1N-(methyl-carboxamidomethyl)-caprolactam-(3S)-amine (2)

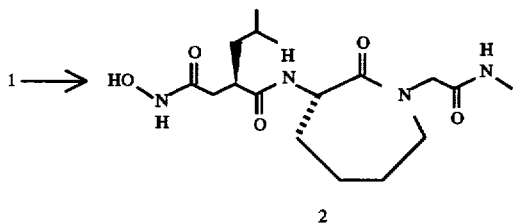

2

(2R)-Isobutyl-3-(N-hydroxycarboxamido)-propionic acid amide of 1N-(methyl-carboxamidomethyl)-caprolactam-(3S)-amine (2). The methyl ester 1 (80 mg, 0.216 mmole) is taken in 5 mL of 8M methyl amine in MeOH and stirred for 15 hours. The solvent is removed and the residue chromatographed over flash silica with EtOAc:formic acid (97:3) to give 2.

EXAMPLE 3

Synthesis of (2R)-Isobutyl-3-(N-hydroxycarboxamido)-propionic acid amide of 1N-(carbo-tert-butoxy-methyl)-caprolactam-(3S)-amine (3)

g, 4.37 mmole) in 5 mL MeOH is added an excess of diazomethane in ether. The excess diazomethane is then quenched with acetic acid and the solvent is evaporated. The residue is chromatographed over flash silica with EtOAc to give the desired ester 30.

(2R)-Isobutyl-3-carbomethoxypropionic acid amide of 1N-(carbo-tert-butoxy-methyl)-caprolactam-(3S)-amine (31). The caprolactam 30 (200 mg, 0.67 mmole) is taken in 5 mL dry tetrahydrofuran ("THF") and cooled to −78° C. under argon. To this solution is added 1M lithium bis (trimethylsilyl)amide (0.67 mL, 0.67 mmole) and the reaction is stirred for 5 min. tert-butyl bromoacetate (99 μL, 0.67 mmole) is added and stirred for 2 hr. The reaction is then partitioned between water and EtOAc. The organic layer is washed with 1N HCl, NaHCO$_3$, and brine, dried over MgSO$_4$, filtered and evaporated to give a crude material which is chromatographed over flash silica with hexanes:EtOAc (1:4) to give pure desired ester 31.

(2R)-Isobutyl-3-(N-hydroxycarboxamido)-propionic acid amide of 1N-(carbo-tert-butoxy-methyl)-caprolactam-(3S)-amine (3). Ester 31 (130 mg, 0.29 mmole) is added to NH$_2$OK (1.3 mL, 1 eq in MeOH, prepared according to Fieser and Fieser, *Reagents for Organic Synthesis*, Vol. 1, p. 478 (1967)) and stirred for 24 hr. The solvent is evaporated and the residue is dissolved in 1N HCl and extracted with EtOAc. The organic layer is dried over MgSO$_4$, evaporated and the residue is chromatographed over flash silica with EtOAc:formic acid (98:2) to give 3.

EXAMPLE 4

Synthesis of (2R)-Isobutyl-3-(N-hydroxycarboxamido)-propionic acid amide of 1N-Benzyl-caprolactam-(3S)-amine (4).

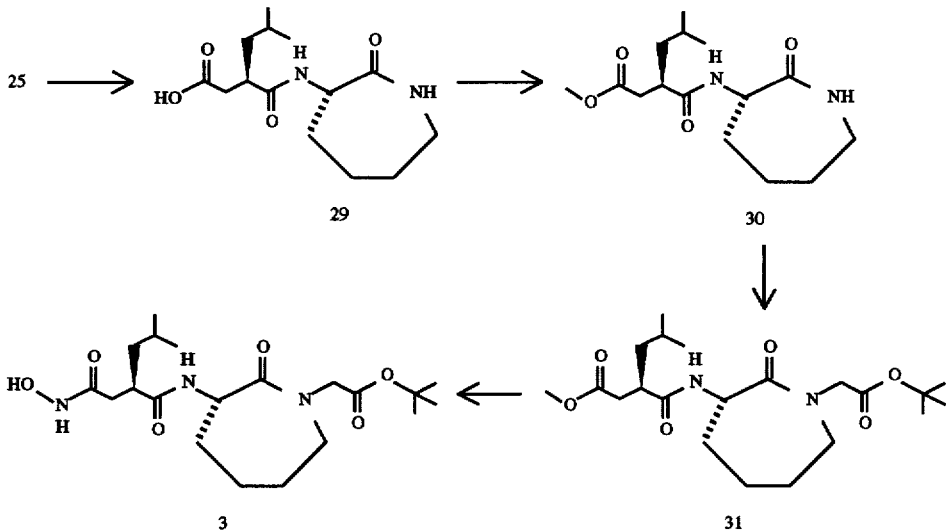

(2R)-Isobutyl-3-carboxypropionic acid amide of caprolactam-(3S)-amine (29)

Trifluoroacetic acid (15 mL) is added via syringe to a solution of tert-butyl ester 25 (2.2 g, 6.47 mmole) in 15 mL CH$_2$Cl$_2$ under argon and the resulting mixture is stirred for 2 hr at room temperature. The material is then concentrated under vacuum to give 29 which is carried forward without purification.

(2R)-Isobutyl-3-carbomethoxypropionic acid amide of caprolactam-(3S)-amine (30). To a solution of acid 29 (1.24

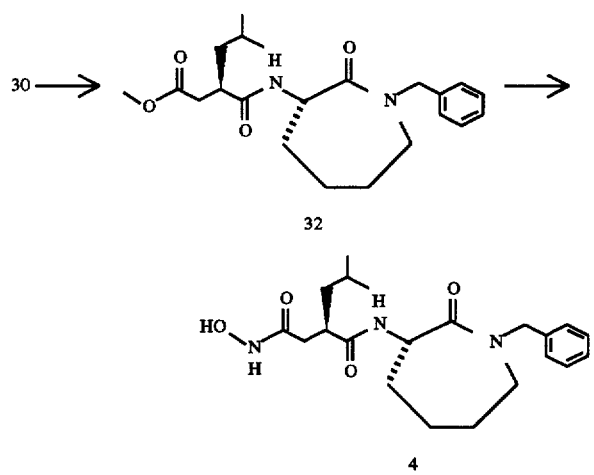

(2R)-Isobutyl-3-carbomethoxypropionic acid amide of 1N-Benzylcaprolactam-(3S)-amine (32). The caprolactam 30 (200 mg, 0.67 mmole) is taken in 5 mL dry THF and is cooled to −78° C. under argon. To this is added 1M lithium bis(trimethylsilyl)amide (0.67 mL, 0.67 mmole) and the reaction stirred for 5 min. Benzyl bromide (80 μL, 0.67 mmole) is added and stirred for 2 hr. The reaction is then partitioned between water and EtOAc. The organic layer is washed with 1N HCl, NaHCO₃, and brine, dried over MgSO₄, filtered and evaporated to give a crude oil which is chromatographed over flash silica with hexanes:EtOAc (1:4) to give 32.

(2R)-Isobutyl-3-(N-hydroxycarboxamido)-propionic acid amide of 1N-Benzyl-caprolactam-(3S)-amine (4). Ester :12 (200 mg, 0.52 mmole) is added to is added to NH₂OK (1.0 mL, 1 eq in MeOH, prepared according to Fieser and Fieser, Vol 1, p 478) and stirred for 24 hr. The solvent is evaporated and the residue is dissolved in 1N HCl and extracted with EtOAc. The organic layer is dried over MgSO₄, evaporated, and the residue is chromatographed over flash silica with EtOAc:formic acid (98:2) to give 4.

EXAMPLE 5

Synthesis of(2R)-Isobutyl-3-N-hydroxycarboxamidopropionic acid amide of 1N-(carbobenzyloxy-methyl)-caprolactam-(3 S)-amine (5)

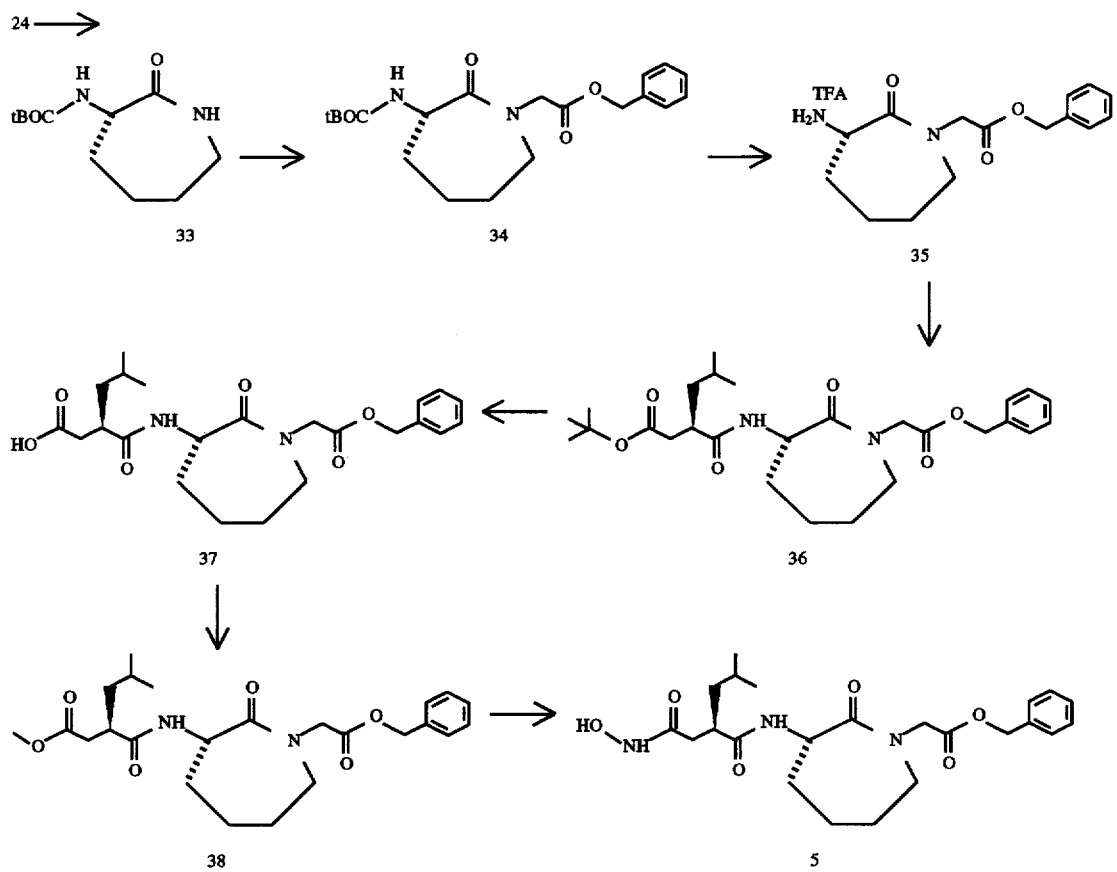

tert-Butoxycarboxylic acid amide of caprolactam-(3S)-amine (33). A solution of 24 (49.0 g, 383 mmole) in 350 mL DMSO is charged with di-tert-butyl dicarbonate (83.5 g, 383 mmole) and stirred for 5 hr at room temperature. The reaction is then partitioned between water and EtOAc. The organic layer is then washed with 1N HCl, and brine, dried over MgSO₄, filtered and evaporated. The residue is recrystallized from ether:hexanes (2:1) to give 33.

tert-Butoxycarboxylic acid amide of 1N-(carbobenzyloxymethyl)-caprolactam-(3S)-amine (34). Lithium bis(trimethylsilyl)amide (44.7 mL, 44.7, 1M in THF) is added to a solution of the caprolactam 33 (10.2 g, 44.7 mmol in THF (100 mL) at −78° C. under argon and stirred for 15 min. Benzyl bromoacetate (7.08 mL, 44.7 mmol) is added to the solution via syringe, warmed to room temperature, and stirred for 2 hr. The reaction is partitioned between H₂O and EtOAc. The organic layer is washed with aqueous NaHCO₃, aqueous NaCl, and dried over MgSO₄. The crude product is chromatographed on flash silica with hexane:EtOAc (1:1) to give 34.

1N-(carbobenzyloxymethyl)-caprolactam-(3S)-amine trifluoroacetic acid salt (35). Trifluoroacetic acid (15 mL) is added via syringe to a solution of tert-butyl carboxamate 34 (5.0 g, 13.2 mmole) in 15 mL under argon and the resulting mixture is stirred for 1 hr at room temperature. The material is then concentrated under vacuum to give 35 which is carried forward without purification.

(2R)-Isobutyl-3-carbo-tert-butoxypropionic acid amide of 1N-(carbobenzyloxy-methyl)-caprolactam-(3S)-amine (36). A mixture of acid 23 (1.67, 7.25 mmole), caprolactam 35 (2.0 g, 7.25 mmole) and HOBT (2.94 g, 21.75 mmole) in 15 mL of DMF and 1.5 mL of NMM is charged with EDAC (1.67 g, 8.70 mmole) and the reaction is stirred for 15 hr at room temperature. The reaction is then partitioned between water and EtOAc and then washed with 1N HCl, NaHCO₃, and brine, dried over MgSO₄, filtered, evaporated and chromatographed over flash silica with EtOAc:hexanes (2:1) to give pure desired amide 36.

(2R)-Isobutyl-3-carbomethoxypropionic acid amide of 1N-(carbobenzyloxy-methyl)-caprolactam-(3S)-amine (38). Trifluoroacetic acid (5 mL) is added via syringe to a solution of tert-butyl ester 36 (1.2 g, 2.46 mmole) in 5 mL of CH₂Cl₂ under argon and the resulting mixture is stirred for 2 hr at room temperature. The material is then concentrated under vacuum to give acid 37 as a clear oil which is carried forward without purification.

To a solution of acid 37 (1.06 g, 2.46 mmole) in 5 mL MeOH is added an excess of diazomethane in ether. The excess diazomethane is then quenched with acetic acid and the solvent evaporated. The residue is chromatographed over flash silica with EtOAc:hexanes (2:1) to give the desired ester 38.

(2R)-Isobutyl-3-N-hydroxycarboxamidopropionic acid amide of 1N-(carbobenzyloxy-methyl)-caprolactam-(3S)-amine (5). Ester 38 (420 mg, 0.94 mmole) is added to a solution of NH₂OK (1.3 mL, 1 eq in MeOH, prepared according to Fieser and Fieser, Vol 1, p 478) and stirred for 24 hours. The solvent is then evaporated and the residue dissolved in 1N HCl and extracted with EtOAc. The organic layer is dried over MgSO₄, evaporated and the residue chromatographed over flash silica with EtOAc:formic acid (98:2) to give 5.

EXAMPLE 6

Synthesis of (2R)-Isobutyl-3-(N-hydroxycarboxamido)-propionic acid amide of 1N-(N-Benzyl-carboxamidomethyl)-caprolactam-(3S)-amine (6)

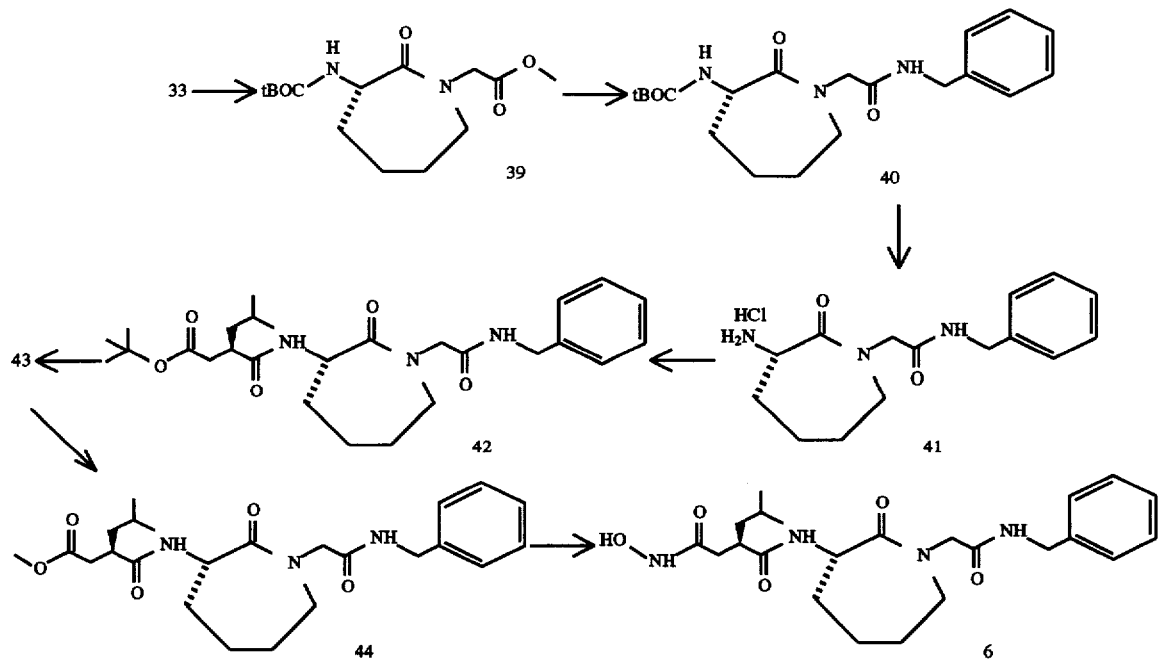

tert-Butoxycarboxylic acid amide of 1N-(carbomethoxymethyl)-caprolactam-(3S)-amine (39). Lithium bis(trimethylsilyl)amide (83.3 mL, 83.3, 1M in THF) is added to a solution of the caprolactam 33 (19.0 g, 83.3 mmol) in THF (200 mL) at −78° C. under argon and stirred for 15 min. Methyl bromoacetate (7.88 mL, 83.3 mmol) is added to the solution via syringe, warmed to room temperature, and stirred for 1 hr. The reaction is partitioned between H₂O and EtOAc. The organic layer is washed with aqueous NaHCO$_3$, aqueous NaCl, and dried over MgSO$_4$. The crude product is chromatographed on flash silica with EtOAc to give 39.

tert-Butoxycarboxylic acid amide of 1N-(N-benzylcarboxamidomethyl)-caprolactam-(3S)-amine (40). The methyl ester 39 (2.5 g, 8.33 mmole) is taken in 10 mL MeOH and the mixture is charged with benzyl amine (8.7 mL, 79.7 mmole) and is stirred for 15 hours. The solvent is removed and the residue is chromatographed over flash silica with EtOAc:hexane (1:1) to give 40.

1N-(N-Benzylcarboxamidomethyl)-caprolactam-(3S)-amine hydrochloride (41).

The amide 40 (2.2 g, 5.87 mmole) is taken in 50 mL ether at 0° C and dry HCl is bubbled through for 10 min. The solid is filtered and washed with ether to give 41.

(3S)-amine (6). Ester 44 (800 mg, 1.80 mole) is added to a solution of NH$_2$OK (1.5 mL, 1 eq in MeOH, prepared according to Fieser and Fieser, Vol 1, p 478) and stirred for 24 hours. The solvent is evaporated and the residue is dissolved in 1N HCl and extracted with EtOAc. The organic layer is dried over MgSO$_4$, filtered, evaporated and the residue is chromatographed over flash silica with EtOAc:formic acid (97:3) to give 6.

EXAMPLE 7

Synthesis of (2R)-Isobutyl-3-N-hydroxycarboxamidopropionic acid amide of 1N-(n-butylcarboxamidomethyl)-caprolactam-(3S)-amine (7)

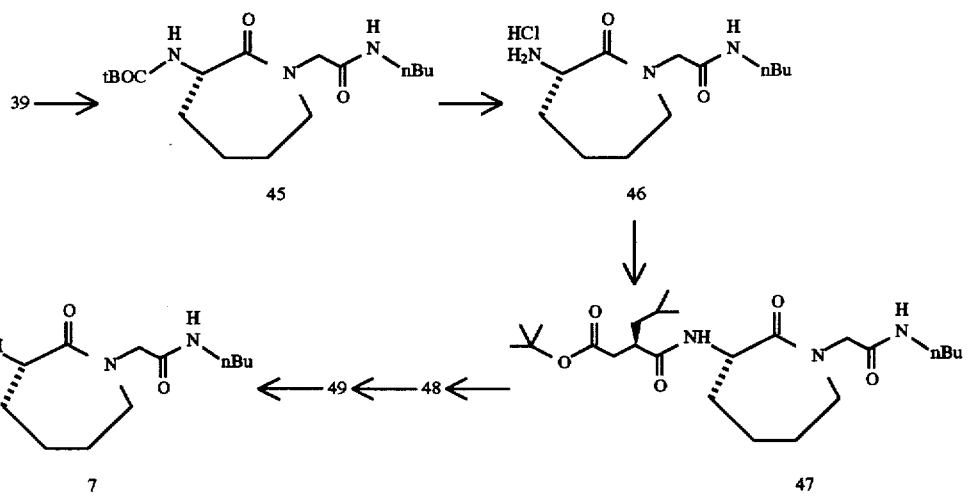

(2R)-Isobutyl-3-carbo-tert-butoxypropionic acid amide of 1N-(N-benzylcarboxamido-methyl)-caprolactam-(3S)-amine (42). A mixture of acid 23 (1.0 g, 4.35 mmole), caprolactam 41 (1.35 g, 4.35 mmole) and HOBT (2.0 g, 13.0 mmole) in 15 mL of DMF and 1.3 mL of NMM is charged with EDAC (1.0 g, 5.22 mmole) and the reaction is stirred for 15 hr at room temperature. The reaction is then partitioned between water and EtOAc. The organic layer is then washed with 1N HCl, NaHCO$_3$, and brine, dried over MgSO$_4$ filtered and evaporated to give 1.9 g of crude solid which is chromatographed over flash silica with EtOAc to give 42.

(2R)-Isobutyl-3-carboxypropionic acid amide of 1N-(N-benzylcarboxamidomethyl)-caprolactam-(3S)-amine (43). Trifluoroacetic acid (5 mL) is added via syringe to a solution of tert-butyl ester 42 (1.51 g, 3.10 mmole) in 5 mL CH$_2$Cl$_2$ under argon and the resulting mixture is stirred for 2 hr at room temperature. The material is then concentrated under vacuum to give 43 which is carried forward without purification.

(2R)-Isobutyl-3-carbomethoxypropionic acid amide of 1N-(N-benzylcarboxamido-methyl)-caprolactam-(3S)-amine (44). To a solution of acid 43 (1.51 g, 3.50 mmole) in 5 mL MeOH is added an excess of diazomethane in ether. The excess diazomethane is quenched with acetic acid and the solvent evaporated. The residue is chromatographed over flash silica with EtOAc:hexanes (2:1) to give 44.

(2R)-Isobutyl-3-(N-hydroxycarboxamido)-propionic acid amide of 1N-(N-benzylcarboxamidomethyl)-caprolactamtert-Butoxycarboxylic acid amide of 1N-(n-butylcarboxamidomethyl)-caprolactam-(3S)-amine (45). The methyl ester 39 (2.5 g, 8.33 mmole) is taken in 10 mL MeOH and the mixture is charged with butyl amine (8.1 mL, 79.7 mmole) and stirred for 15 hr. The solvent is removed and the residue is chromatographed over flash silica with EtOAc:hexane (2:1) to give 45.

1N-(n-butylcarboxamidomethyl)-(3S)-aminocaprolactam hydrochloride (46). The amide 45 (2.2 g, 6.43 mmole) is taken in 50 mL ether at 0° C. and dry HCl is bubbled through for 10 min. The solid is filtered and washed with ether to give 46.

(2R)Isobutyl-(3)-carbo-tert-butoxypropanoic acid amide of (1N)-n-butylcarboxamido-methyl-caprolactam-(3S)-amine (47). A mixture of acid 23, (1.76 g, 7.65 mmole), 1N-(n-butylcarboxamidomethyl)-caprolactam-(3S)-amine 46 (3.17 g, 11.4 mmole) and HOBT (3.08 g. 22.80 mmole) in 20 mL of DMF and 2.36 mL of NMM is charged with EDAC (1.74 g, 9.07 mmole) and the reaction is stirred for 15 hr at room temperature. The reaction is then partitioned between water and EtOAc. The organic layer is then washed with 1N HCl, NaHCO$_3$, and brine, dried over MgSO$_4$, filtered and evaporated to give 4.68 g of crude solid which is chromatographed over flash silica with EtOAc to give 47.

(2R)-Isobutyl-(3)-carboxypropanoic acid amide of (1N)-n-butylcarboxamidomethyl-caprolactam-(3S)-amine (48). Trifluoroacetic acid (15 mL) is added via syringe to a solution of the tert-butyl ester 47 (2.45 g, 5.40 mmole) in 15 mL of CH$_2$Cl$_2$ under argon and the resulting mixture is stirred for 1 hr at room temperature. The material is then concentrated under vacuum to give 48 which is carried forward without purification.

(2R)-Isobutyl-3-carbomethoxypropionic acid amide of 1N-(n-butylcarboxamidomethyl)-caprolactam-(3S)-amine (49). The acid 48 (1.23 g, 3.09 mmole) is taken in methanol and treated with an excess of diazomethane in ether at 0° C., and stirred for one hour. Formic acid (3 drops) is added and the mixture is evaporated to dryness to give 49 which is carried forward without purification.

(2R)-Isobutyl-3-N-hydroxycarboxamidopropionic acid amide of 1N-(n-butyl-carboxamidomethyl)-caprolactam-(3S)-amine (7). The methyl ester 49 (500 mg, 1.21 mmole) is added to a solution of NH₂OK (1.4 mL, 1 eq in MeOH, prepared according to Fieser and Fieser, Vol 1, p 478) and stirred for 15 hr. The reaction mixture is acidified with acetic acid to pH=2. The reaction is then partitioned between ethyl acetate and water. The organic layer is then washed with brine, and dried over magnesium sulfate, filtered and evaporated to give a crude solid which is chromatographed with ethyl acetate:water:acetic acid (16:1:1) and then recrystallized from ethyl acetate to give 7.

EXAMPLE 8

Synthesis of (2R)-N-Hydroxycarboxamidomethyl heptanoic acid amide of N-(carbomethoxymethyl)-caprolactam-(3S)-amine (8)

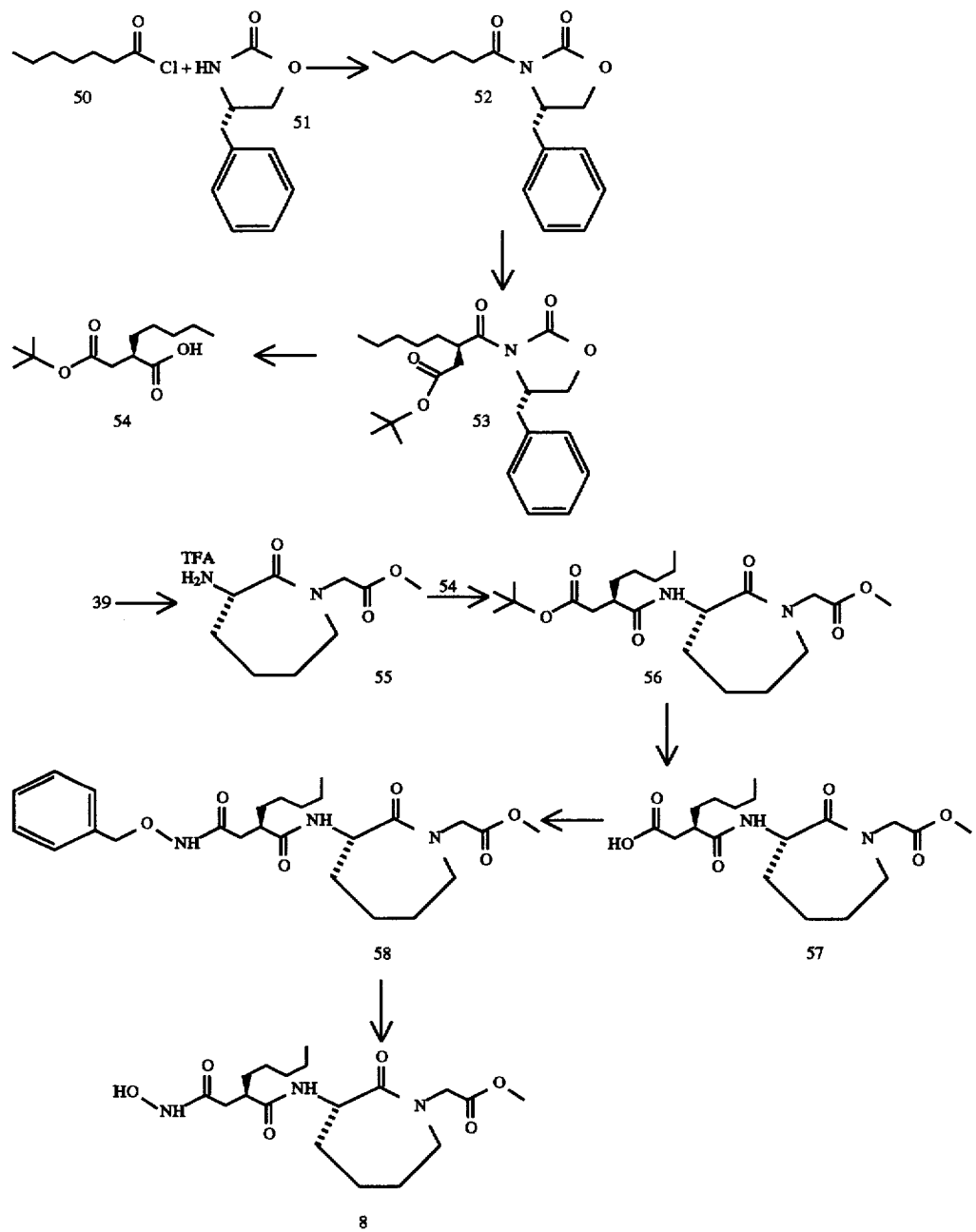

3-(1-Oxoheptyl)-(4S)-phenylmethyl-2-oxazolidinone (52). n-Butyl lithium (58 mL, 2.5M in hexanes, 142 mmol) is added to a solution of (S)-4-benzyl-2-oxazolidinone 51 (25 g, 141 mmol) in THF (250 mL) at −78° C. under argon and stirred for 15 min. Heptanoyl chloride 50 (21 g, 141 mmol) is added to the solution dropwise and stirred for 40 min, then warmed to 0° C. for 2 hours. The reaction is quenched with NH$_4$Cl and extracted with EtOAc. The organic layer is washed with 1N HCl, aqueous NaHCO$_3$, aqueous NACl, and dried over MgSO$_4$. The crude product is recrystallized from hexane to give 52.

3-[1-Oxo-(2R-(carbo-tert-butoxymethyl)-heptyl]-(4S)-phenylmethyl-2-oxazolidinone (53). Lithium bis (trimethylsilyl)amide (132 mL, 132 mmol, 1M in THF) is added to a solution of the oxazolidinone 52 (38.0 g, 132 mmol) in THF (100 mL) at −78° C. under argon and stirred for 15 min. tert-Butyl bromoacetate (26 mL, 132 mmol) is added to the solution via syringe and stirred for 3 hr. The reaction is then warmed to 0° C. and stirred for 1.5 hr. The reaction is quenched with NH$_4$Cl and extracted with EtOAc. The organic layer is washed with 1N HCl, aqueous NaHCO$_3$, aqueous NaCl, and dried over MgSO$_4$. The crude product is recrystallized from hexane:EtOAc (2:1) to give 53.

tert-Butyl-[(3R)-carboxy]octanoate (54). The oxazolidinone 53 (10.0 g, 24.9 mmole) is dissolved in THF/H$_2$O (100 mL: 25 mL) under argon and cooled to 0° C. Hydrogen peroxide (12 mL, 30%, 106.7 mmol) is added dropwise to the solution, followed by lithium hydroxide monohydrate (1.8 g, 43.9 mmol) in H$_2$O (40 mL). The reaction is stirred for 3 hr, at which time sodium sulfite (10 g in 40 mL H$_2$O ) is added dropwise and stirred for 20 min. The solution is extracted 3 times with CH$_2$Cl$_2$. The organic extracts are combined, washed with aqueous NaCl, dried over MgSO$_4$, filtered, and the solvent removed to give 54.

1N-(carbomethoxymethyl)-caprolactam-(3S)-amine trifluoroacetic acid salt (55).

Trifluoroacetic acid (15 mL) is added via syringe to a solution of tert-butyl carboxamate 39 (10.0 g, 33.3 mmole) in 15 mL under argon and the resulting mixture is stirred for 1 hr at room temperature. The material is then concentrated under vacuum to give 55 which is carried forward without purification.

(2R) -Carbo-tert-butoxymethyl heptanoic acid amide of N-carbomethoxymethyl-caprolactam-(3S)-amine (56). The amine 55 (2.16 g, 10.8 mmole) is mixed with the acid 54 (2.64 g, 10.8 mmole), HOBT (4.4 g, 32.4 mmole), EDAC (2.69 g, 14 mmole) in 15 mL of DMF and 2.4 mL (21.6 mmole) of NMM at 0° C., and stirred for 17 hr at room temperature. The reaction is then partitioned between water and EtOAc. The organic layer is washed with 1N HCl, H$_2$O, 1N NaOH, and brine, dried over MgSO$_4$, filtered and evaporated to give an oil (3.2 g) which is chromatographed over flash silica with hexane:EtOAc (1:1) to give 56.

(2R)-O-Benzyl-N-hydroxycarboxamidomethyl heptanoic acid amide of N-carbomethoxymethyl-caprolactam-(3S)-amine (58). The ester 56 (1.2 g, 2.64 mmole) is dissolved in 15 mL of methylene chloride and cooled to 0° C. and trifluoroacetic acid (15 mL) is added slowly. The mixture is stirred for 1.5 hr at room temperature and evaporated to 57.

A mixture of the crude acid 57 (1.5 g, 2.64 mmole ), O-benzyl hydroxylamine hydrochloride (0.51 g, 3.17 mmole) and HOBT (1.07 g, 7.92 mmole) in 10 mL of DMF and 0.99 mL of NMM (9.0 mmole) is charged with EDAC (0.61 g, 3.17 mmole) and the reaction is stirred for 15 hr at room temperature. The reaction is then partitioned between water and EtOAc. The organic layer is then washed with 1N HCl, NaHCO$_3$, and brine, dried over MgSO$_4$, filtered and evaporated to give an oil which is chromatographed over flash silica with EtOAc to give 58.

(2R)-N-Hydroxycarboxamidomethyl heptanoic acid amide of N-(carbomethoxymethyl)-caprolactam-(3S)-amine (8). The benzyl hydroxamic acid 58 (370 mg, 0.78 mmole) is taken in 10 mL of EtOH and the mixture is charged with 10% palladium on carbon (44 mg) and stirred under one atmosphere of hydrogen for 3 hr. The mixture is then filtered through celite and concentrated to an oil. The crude product is crystallized from ethyl acetate to give 8.

EXAMPLE 9

Synthesis of(2R)-N-hydroxycarboxamidemethyldecanoic acid amide of 1N-(carbomethoxymethyl)-caprolactam-(3S)-amine (9)

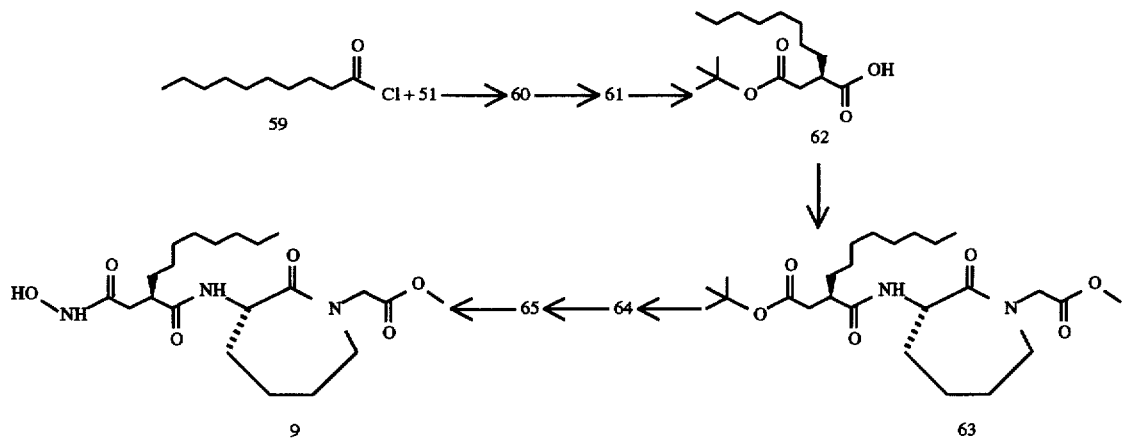

3-(1-Oxodecyl)-(4S)-phenylmethyl-2-oxazolidinone (60). n-Butyl lithium (160 mL, 398 mmol, 2.5M in hexanes) is added to a solution of (S)-4-benzyl-2-oxazolidinone 51 (64 g, 362 mmol) in THF (750 mL) at −78° C. under argon and stirred for 15 min. Decanoyl chloride 59 (69 g, 362 mmol) is added to the solution dropwise and stirred for 40 min, then warmed to 0° C. for 2 hours. The reaction is quenched with NH$_4$Cl and extracted with EtOAc. The organic layer is washed with 1N HCl, aqueous NaHCO$_3$, aqueous NaCl, and dried over MgSO$_4$. The crude product is recrystallized from hexane to give 60.

3-[1-Oxo-(2R)-(carbo-tert-butoxymethyl)-decyl]-(4S)-phenylmethyl-2-oxazolidinone (61). Lithium bis(trimethylsilyl)amide (210 mL, 1M in THF, 210 mmol) is added to a solution of the oxazolidinone 60 (66.6 g, 200 mmol) in THF (100 mL) at −78° C. under argon and stirred for 15 min. tert-Butyl bromoacetate (31 mL, 200 mmol) is added to the solution via syringe and stirred for 3 hr. The reaction is warmed to 0° C. and stirred for 1.5 hr. The reaction is quenched with NH$_4$Cl and extracted with EtOAc. The organic layer is washed with 1N HCl, aqueous NaHCO$_3$, aqueous NaCl, and dried over MgSO$_4$. The crude product is chromatographed on flash silica with hexane:EtOAc (7:1) to give 61.

tert-Butyl-[3R-carboxy]undecanoate (62). Oxazolidinone 61 is dissolved in THF/H$_2$O (100 mL:25 mL) under argon and cooled to 0° C. Hydrogen peroxide (13 mL, 30%, 115.6 mmol) is added dropwise to the solution, followed by lithium hydroxide monohydrate (1.8 g, 43.9 mmol) in H$_2$O (40 mL). The reaction is stirred for 3 hr, at which time sodium sulfite (10 g in 40 mL H$_2$O) is added dropwise and stirred 20 min. The solution is extracted 3 times with CH$_2$Cl$_2$. The organic extracts are combined, washed with trated under vacuum to give 64 which is carried forward without purification.

A mixture of acid 64 (1.05 g, 2.55 mmole), O-benzyl hydroxylamine hydrochloride (165 mg, 2.55 mmole) and HOBT (1.2 g, 7.65 mmole) in 15 mL of DMF and 6 mL of NMM is charged with EDAC (572 mg, 2.55 mmole) and the reaction is stirred for 15 hr at room temperature. The reaction is then partitioned between water and EtOAc. The organic layer is then washed with 1N HCl, NaHCO$_3$, and brine, dried over MgSO$_4$, filtered, evaporated and chromatographed over flash silica with EtOAc to give 65.

(2R)-N-hydroxycarboxamidemethyldecanoic acid amide of 1N-(carbomethoxy-methyl)-caprolactam-(3S)-amine (9). The benzyl hydroxamic acid 65 (428 mg, 0.828 mmole) is taken in 15 mL EtOH and the mixture is charged with 10% palladium on carbon (60 mg) and stirred under one atmosphere of hydrogen for 45 min. The mixture is then filtered through celite and concentrated and chromatographed over flash silica with EtOAc:formic acid (99:1) and then recrystallized from EtOAc to give 9.

EXAMPLE 10

Synthesis of (2R)-N-Hydroxycarboxamidomethyl decanoic acid amide of N-p-toluenesulfonyl-caprolactam-(3S)-amine (10)

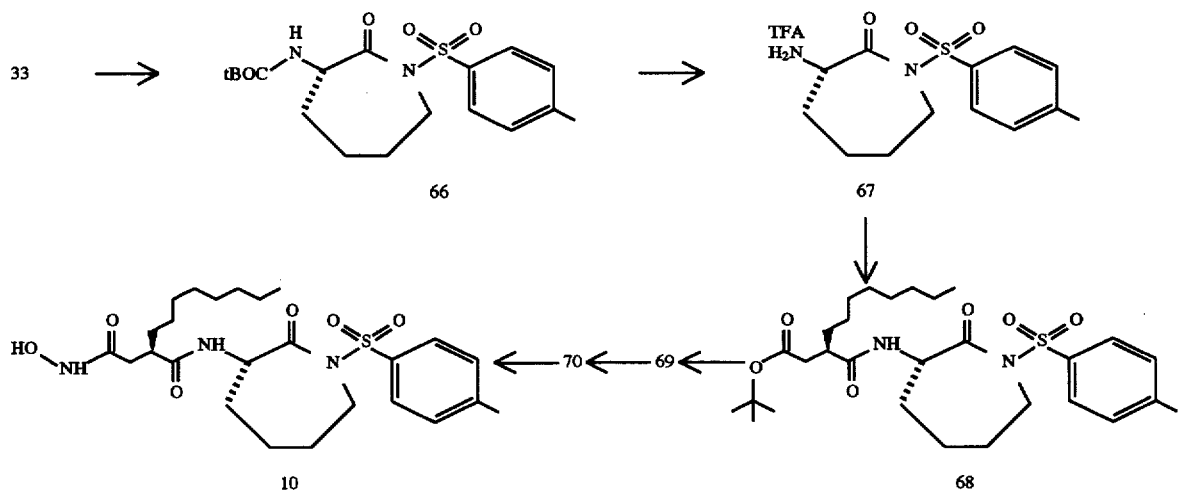

aqueous NaCl, and dried over MgSO$_4$. The product is purified on a silica gel column using EtOAc as the eluent to give 62.

(2R)-Carbo-tert-butoxymethyldecanoic acid amide of 1N-(carbomethoxymethyl)-caprolactam-(3S)-amine (63). A mixture of acid 62 (2.5 g, 8.74 mmole) and 0.9 mL NMM is cooled to −20° C. and charged with isobutyl chloroformate (1.45 mL, 8.74 mmole) and stirred for 10 min. The amine 55 (1.75 g, 8.74 mmole) and 0.9 mL NMM in 2 mL DMF is added and stirred for 30 min. The reaction is then partitioned between water and EtOAc. The organic layer is then washed with 1N HCl, NaHCO$_3$, and brine, dried over MgSO$_4$, filtered and evaporated to give 2.8 g of crude solid which chromatographed over flash silica with EtOAc:hexanes (1:1) to give 63.

(2R)-O-Benzyl-N-hydroxycarboxamidemethyldecanoic acid amide of 1N-(carbomethoxymethyl)-caprolactam-(3S)-amine (65). Trifluoroacetic acid (5 mL) is added via syringe to a solution of tert-butyl ester 63 (1.2 g, 2.56 mmole) in 5 mL CH$_2$Cl$_2$ under argon and the resulting mixture is stirred for 2 hr at room temperature. The material is then concen- (3S)-tert-Butoxycarbonylamino-N-toluenesulfonyl-caprolactam (66). (3S)-tert-Butoxy-carbonylamino caprolactam 33 (2.0 g, 8.8 mmole) is dissolved in THF (20 mL) and cooled to 0° C. A solution of lithium bis(trimethylsilyl) amide (10.6 mL, 10.6 mmole, 1M in THF) is added dropwise. After 15 min, toluenesulfonyl chloride (2.0 g, 10.56 mmole) is added. The resulting mixture is stirred at 0° C. for 10 min and room temperature for 30 min. The reaction is quenched by water and extracted by ethyl acetate. The organic layer is then washed with 0.1N HCl, H$_2$O, and brine, dried over MgSO$_4$, filtered and evaporated to give an oil which is chromatographed over flash silica with hexanes:EtOAc 0:1) to give 66.

(2R)-Carbo-tert-butoxymethyl decanoic acid amide of N-toluenesulfonyl-caprolactam-(3S)-amine (68). (3S)-tert-Butoxycarbonylamino-N-toluenesulfonyl-caprolactam 66 (2.2 g, 5.8 mmole) is dissolved in 10 mL of methylene chloride and trifluoroacetic acid (10 mL) is added slowly. The mixture is stirred for 30 min. and evaporated to give 67.

The caprolactam amine 67 (1.6 g, 5.7 mmole) is mixed with 62, HOBT (2.31 g, 17.1 mmole), EDAC (1.34 g, 7 mmole) in 25 mL of DMF and 1.26 mL (11.4 mmole) of NMM at 0° C., and stirred for 17 hr at room temperature. The reaction is then partitioned between water and EtOAc. The organic layer is washed with 1N HCl, NaHCO₃, and brine, dried over MgSO₄, filtered and evaporated to give an oil (3.1 g) which is chromatographed over flash silica with EtOAc to give 68.

(2R)-O-Benzyl-N-hydroxycarboxamidomethyl decanoic acid amide of N-toluenesulfonyl-caprolactam-(3S)-amine (70). (3S)-tert-Butoxycarbonylamino-N-toluenesulfonyl-caprolactam 68 (2.1 g, 3.8 mmole) is dissolved in 10 mL of methylene chloride, cooled to 0° C., and trifluoroacetic acid (10 mL) is added slowly. The mixture is stirred for 1.5 hr at room temperature and evaporated to give 69.

A mixture of the crude acid 69 (2 g, 3.8 mmole), O-benzyl hydroxylamine hydrochloride (0.73 g, 4.56 mmole) and HOBT (1.54 g. 11.4 mmole) in 20 mL of DMF and 1.4 mL of NMM (12.9 mmole) is charged with EDAC (0.87 g, 4.56 mmole) and the reaction is stirred for 15 hr at room temperature. The reaction is then partitioned between water and EtOAc. The organic layer is washed with 1N HCl, 1N NaOH, and brine, dried over MgSO₄, filtered and evaporated to give a semisolid (2.2 g) which is chromatographed over flash silica with EtOAc:hexane (1:1) to give 70.

(2R)-N-Hydroxycarboxamidomethyl decanoic acid amide of N-toluenesulfonyl-caprolactam-(3S)-amine (10). The benzyl hydroxamic acid 70 (680 mg, 1.13 mmole) is taken in 10 mL of EtOH and the mixture is charged with 10% palladium on carbon (68 mg) and stirred under one atmosphere of hydrogen for 2.5 hr. The mixture is filtered through celite and concentrated to give a solid, which is purified by flash chromatography (silica, EtOAc) to give 10.

EXAMPLE 11

Synthesis of 2R)-N-Hydroxycarboxamidomethyl decanoic acid amide of N-[(2-methoxy)ethyl]-caprolactam-(3S)-amine (11)

water and extracted with ethyl acetate. The organic layer is then washed with 1N HCl, H₂O, and brine, dried over MgSO₄, filtered and evaporated to give an oil which is chromatographed over flash silica with hexanes:EtOAc (1:1) to give 71.

(2R)-Carbo-tert-butoxymethyl decanoic acid amide of N-[(2-methoxy)ethyl]-caprolactam-(3S)-amine (73). (3S)-tert-Butoxycarbonylamino-N-[(2-methoxy)ethyl]-caprolactam 71 (1.46 g, 5.1 mmole) is dissolved in 15 mL of methylene chloride, cooled to 0° C., and trifluoroacetic acid (15 mL) is added slowly. The mixture is stirred for 2 hr at room temperature and evaporated to 72.

The caprolactam amine 72 is mixed with (2R)-tert-Butylcarboxymethyl decanoic acid (1.5 g, 5.2 mmole), HOBT (2.07 g, 15.3 mmole), EDAC (1.17 g, 6.1 mmole) in 15 mL of DMF and 1.43 mL (13 mmole) of NMM at 0° C., and stirred for 17 hr at room temperature. The reaction is then partitioned between water and EtOAc. The organic layer is washed with 1N HCl, H₂O, 1N NaOH, and brine, dried over MgSO₄, filtered and evaporated to give an oil which is chromatographed over flash silica with EtOAc to give 73.

(2R)-O-Benzyl-N-hydroxycarboxamidomethyl decanoic acid amide of N-[(2-methoxy)ethyl]-caprolactam-(3S)-amine (75). (3S)-tert-Butoxycarbonylamino-N-[(2-methoxy)ethyl]-caprolactam 73 (1.2 g, 2.64 mmole) is dissolved in 15 mL of methylene chloride, cooled to 0° C., and trifluoroacetic acid (15 mL) is added slowly. The mixture is stirred for 1.5 hr at room temperature and evaporated to give 74.

A mixture of the crude acid 74 (1.5 g, 2.64 mmole), O-benzyl hydroxylamine hydrochloride (0.51 g, 3.17 mmole) and HOBT (1.07 g. 7.92 mmole) in 10 mL of DMF and 0.99 mL of NMM (9.0 mmole) is charged with EDAC (0.61 g, 3.17 mmole) and the reaction is stirred for 15 hr at room temperature. The reaction is then partitioned between water and EtOAc. The organic layer is then washed with 1N HCl, NaHCO₃, and brine, dried over MgSO₄, filtered and

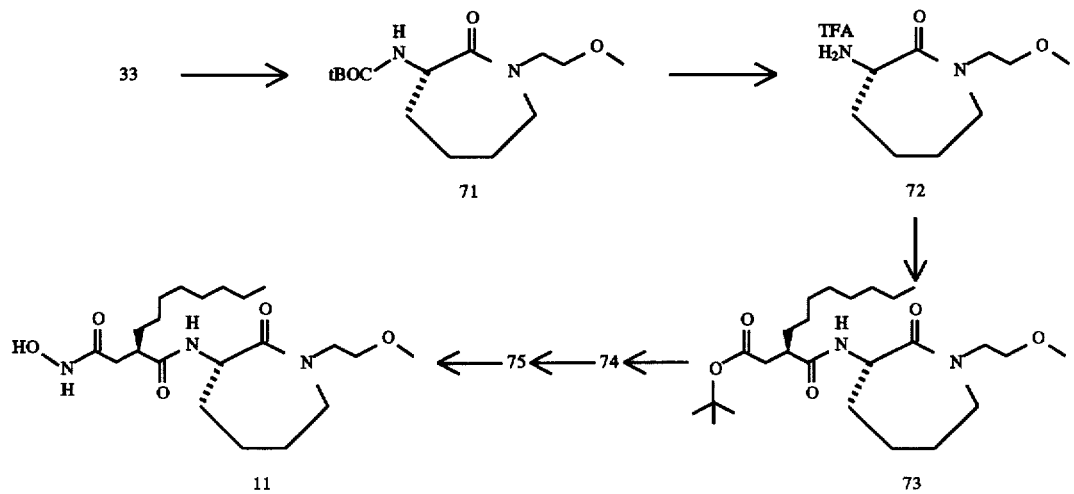

(3S)-tert-Butoxycarbonylamino-N-[(2-methoxy)ethyl]-caprolactam (71). (3S)-tert-Butoxycarbonylamino caprolactam 33 (2.0 g, 8.8 mmole) is dissolved in DMF (10 mL). Potassium tert-butoxide (1.25 g, 10.6 mmole) is added dropwise, and stirred for 45 min. Bromo ethyl methyl ether (0.99 mL, 10.6 mmole) is then added. The resulting mixture is stirred for 3 hr, at which time the reaction is quenched by evaporated to give an oil which is chromatographed over flash silica with EtOAc to give 75.

(2R)-N-Hydroxycarboxamidomethyl decanoic acid amide of N-[(2-methoxy)ethyl]-caprolactam-(3S)-amine (11). The benzyl hydroxamic acid 75 (700 mg, 1.39 mmole) is taken in 10 mL of EtOH and the mixture is charged with 10% palladium on carbon (70 mg) and stirred under one atmosphere of hydrogen for 1.5 hr. The mixture is filtered through celite and concentrated to give a solid, which is purified by flash chromatography (silica, 4% formic acid in EtOAc) to give 11.

EXAMPLE 12

Synthesis of (2R)-N-Hydroxycarboxamidomethyl decanoic acid amide of 1-N-n-butyl-caprolactam-(3S)-amine (12)

3.1 mmole) is dissolved in 15 mL of methylene chloride and cooled to 0° C. and trifluoroacetic acid (15 mL) is added slowly. The mixture is stirred for 1.5 hr at room temperature and evaporated to give 79.

A mixture of the crude acid 79 (1.5 g, 3.1 mmole), O-benzyl hydroxylamine hydrochloride (0.6 g, 3.72 mmole) and HOBT (1.26 g, 9.3 mmole) in 10 mL of DMF and 1.16 mL of NMM (10.5 mmole) is charged with EDAC (0.71 g, 3.72 mmole) and the reaction is stirred for 15 hr at room temperature. The reaction is then partitioned between water

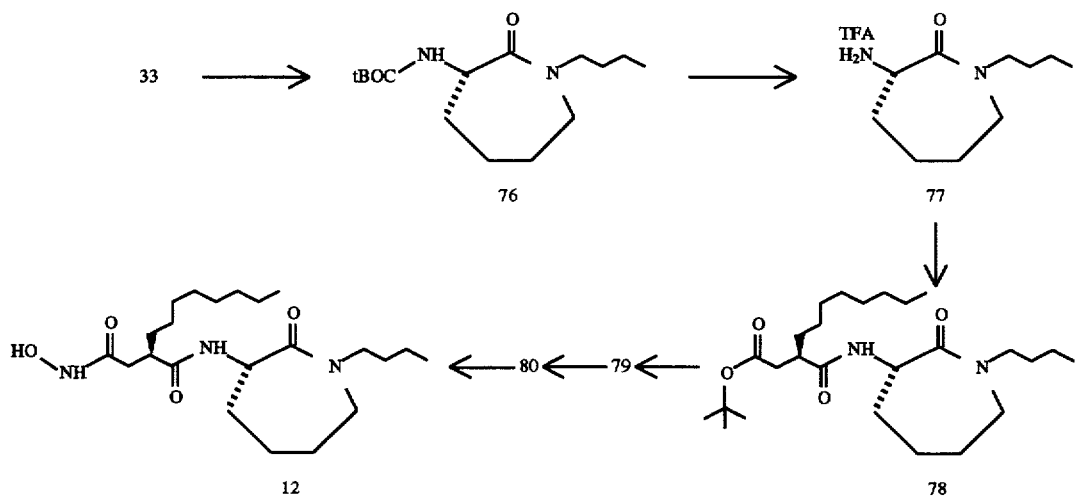

(3S)-tert-Butoxycarbonylamino-N-n-butyl-caprolactam (76). (3S)-tert-Butoxy-carbonylamino caprolactam 33 (2.0 g, 8.8 mole) is dissolved in DMF (8 mL). Potassium tert-butoxide (1.25 g, 10.6 mmole) is added dropwise, and stirred for 50 min. 1-Bromo butane (1.13 mL, 10.6 mmole) is then added. The resulting mixture is stirred for 3 hr, at which time the reaction is quenched with water and extracted with ethyl acetate. The organic layer is then washed with 1N HCl, H₂O, and brine, dried over MgSO₄, filtered and evaporated to give an oil which is chromatographed over flash silica with hexanes:EtOAc (1:1) to give 76.

(2R)-carbo-tert-butoxymethyl decanoic acid amide of N-n-butyl-caprolactam-3S)-amine (78). 76 (2.37 g, 8.3 mmole) is dissolved in 15 mL of methylene chloride, cooled to 0° C., and trifluoroacetic acid (15 mL) is added slowly. The mixture is stirred for 2 hr at room temperature and evaporated to give 77.

The caprolactam amine 77 is mixed with 62 (1.5 g, 5.2 mmole), HOBT (3.36 g, 24.9 mmole), EDAC (1.92 g, 10 mmole) in 15 mL of DMF and 2.3 mL (20.8 mmole) of NMM at 0° C., and stirred for 17 hr at room temperature. The reaction is then partitioned between water and EtOAc. The organic layer is washed with 1N HCl, H₂O, 1N NaOH, and brine, dried over MgSO₄, filtered and evaporated to give an oil which is chromatographed over flash silica with EtOAc to give 78.

(2R)-O-Benzylhydroxycarboxamidomethyl decanoic acid amide of N-n-butyl-caprolactam-(3S)-amine (80). 78 (1.4 g, and EtOAc. The organic layer is washed with 1N HCl, 1N NaOH, and brine, dried over MgSO₄, filtered and evaporated to give an oil which is chromatographed over flash silica with EtOAc to give 80.

(2R)-N-Hydroxycarboxamidomethyl decanoic acid amide of 1-N-n-butyl-caprolactam-(3S)-amine (12). The benzyl hydroxamic acid 80 (900 mg, 1.8 mmole) is taken in 10 mL of EtOH and the mixture is charged with 10% palladium on carbon (90 mg) and stirred under one atmosphere of hydrogen for 2 hr. The mixture is filtered through celite and concentrated to give a solid, which is purified by flash chromatography (silica, 2% formic acid in EtOAc). The product is then crystallized from ethyl acetate to give 12.

EXAMPLE 13

(2R)-Isobutyl-(3S)-[N-hydroxycarboxamido]-butanoic acid amide of (1N)-carbomethoxymethyl-caprolactam-(3S)-amine (13)

EXAMPLE 14

(2R)-Isobutyl-(3R)-[N-hydroxycarboxamido]-butanoic acid amide of (1N)-carbomethoxymethyl-caprolactam-(3S)-amine (14)

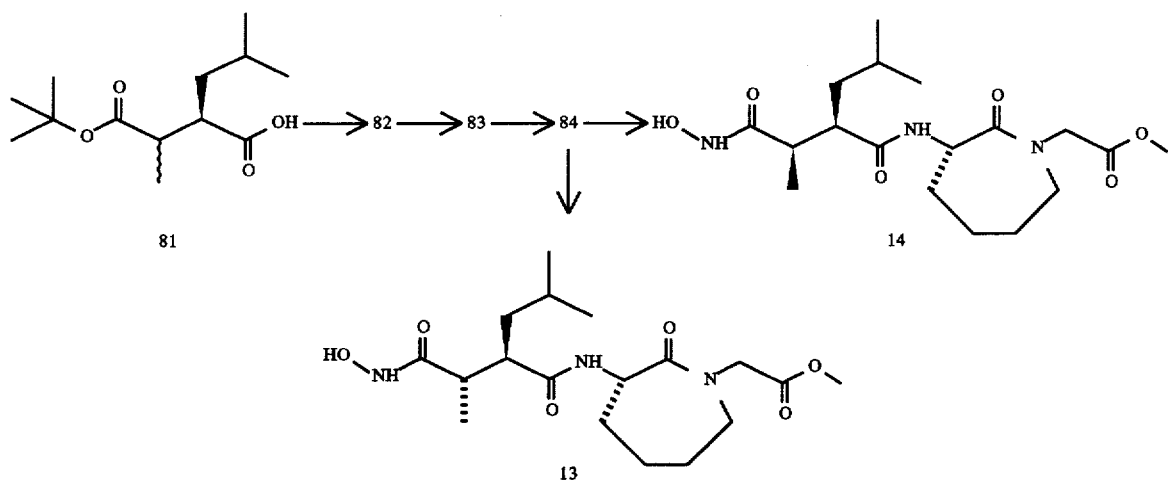

(2R)-Isobutyl-(3R,S)-carbo-tert-butoxybutanoic acid amide of (1N)-carbomethoxymethylcaprolactam-(3S)-amine (82). A mixture of acids 81 (3R:3S=8:1; 720 mg, 2.95 mmole), 55 (767 mg, 3.84 mmole) and HOBT (1.39 g, 10.33 mmole) in 4 mL of DMF and 4 mL of NMM is charged with EDAC (737 mg, 3.84 mmole) and the reaction is stirred for 15 hr at room temperature. The reaction is then partitioned between water and EtOAc. The organic layer is then washed with 1N HCl, NaHCO$_3$, and brine, dried over MgSO$_4$, filtered and evaporated to give a crude solid which is chromatographed over flash silica with hexanes:EtOAc (3:1→1:2) to give 82 (3R:3S=8:1).

(2R)-Isobutyl-(3R,S)-[O-benzyl-N-hydroxycarboxamido]-butanoic acid amide of (1N)-carbomethoxymethyl-caprolactam-(3S)-amine (84). The esters 82 (3R:3S=8:1; 560 mg, 1.31 mmole), are dissolved in 4 mL of CH$_2$Cl$_2$ under argon and to this mixture is added 4 mL of trifluoroacetic acid via syringe. The mixture is stirred for 30 min. at which time the mixture is concentrated to give 83.

A mixture of the resulting crude acid 83 (560 mg, 1.51 mmole), O-benzyl hydroxylmine hydrochloride (314 mg, 1.96 mmole) and HOBT (917 mg, 6.80 mmole) in 4 mL of DMF and 4 mL of NMM is charged with EDAC (376 mg, 1.96 mmole) and the reaction is stirred for 15 hr at room temperature. The reaction is then partitioned between water and EtOAc. The organic layer is then washed with 1N HCl, NaHCO$_3$, and brine, dried over MgSO$_4$, filtered and evaporated. The crude solid is filtered through a plug of silica gel and then recrystallized to give the 84 (3R) diastereomer. The mother liquor is then chromatographed through silica gel with hexanes:EtOAc (1:1→0:1) to give 84 (3S).

(2R)-Isobutyl-(3S)-[N-hydroxycarboxamido]-butanoic acid amide of (1N)-carbomethoxymethyl-caprolactam-(3S)-amine (13). The benzyl hydroxamic acid 84 (3S) (45 mg, 0.095 mmole) is taken in 1 mL 95% EtOH and the mixture is charged with 5 mg of 10% palladium on carbon and stirred under one atmosphere of hydrogen for 12 hours. The mixture is then filtered through celite and concentrated to give a crude oil which is crystallized from EtOAc:EtOH (20:1) to give 13.

(2R)-Isobutyl-(3R)-[N-hydroxycarboxamido]-butanoic acid amide of (1N)-carbomethoxymethyl-caprolactam-(3S)-amine (14). The benzyl hydroxamic acid 84 (3R) (100 mg, 0.211 mmole) is taken in 1.5 mL 95% EtOH and the mixture is charged with 10% palladium on carbon (10 mg) and stirred under one atmosphere of hydrogen for 15 hours. The mixture is then filtered through celite and concentrated to give 14.

EXAMPLE 15

Synthesis of (2R)-Isobutyl-(3S)-[N-hydroxycarboxamido]-hexanoic acid amide of (1N)-carbomethoxymethyl-caprolactam-(3S)-amine (15)

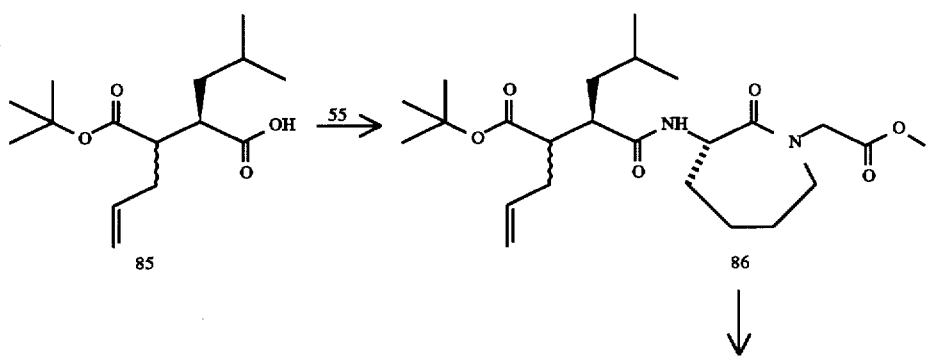

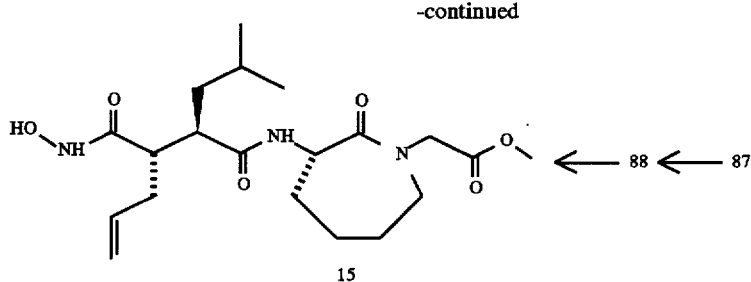

(2R)-Isobutyl-(3S)-[carbo-tert-butoxy]-hex-5-enoic acid amide of (1N)-carbomethoxymethylcaprolactam-(3S)-amine (86). A mixture of acid 85 (1.91 g, 7.07 mmole), 55 (1.84 g, 9.20 mmole) and HOBT (2.77 g, 20.5 mmole) in 2 mL of DMF and 2 mL of NMM is charged with EDAC (2.04 g, 10.6 mmole) and the reaction is stirred for 15 hr at room temperature. The reaction is then partitioned between water and EtOAc. The organic layer is then washed with 1N HCl, NaHCO$_3$, and brine, dried over MgSO$_4$, filtered and evaporated to give a crude solid which chromatographed over flash silica with hexanes: EtOAc (3:1→1:2) to give 86.

(2R)-Isobutyl-(3R, S)-carboxyhex-5-enoic acid amide of (1N)-carbomethoxymethyl-caprolactam-(3S)-amine (87). Trifluoroacetic acid (15 mL) is added via syringe to a solution of tert-butyl esters 86 (3R:3S=2:3; 1.51 g, 3.34 mmole) in 15 mL of CH$_2$Cl$_2$ under argon and the resulting mixture is stirred for 1 hr at room temperature. The material is then concentrated under vacuum to give 87 as a diastereomeric mixture (3R:3S=2:3) which is carried forward without purification.

(2R)-Isobutyl-(3S)-[O-benzyl-N-hydroxycarboxamido]-hex-5-enoic acid amide of (1N)-carbomethoxymethyl-caprolactam-(3S)-amine (88). A mixture of acids 87 (3R:3S=2:3; 1.32 g, 3.34 mmole), O-benzyl hydroxylamine hydrochloride (0.693 g, 4.34 mmole) and HOBT (1.26 g, 9.35 mmole) in 7 mL of DMF and 7 mL of NMM is charged with EDAC (0.962 mg, 5.01 mmole) and the reaction is stirred for 15 hr at room temperature. The reaction is then partitioned between water and EtOAc. The organic layer is then washed with 1N HCl, NaHCO$_3$, and brine, dried over MgSO$_4$, and evaporated to give a crude solid which is filtered through a plug of silica gel with EtOAc and then recrystallized 2x from hexanes:EtOAc (2:1) to give 88.

(2R)-Isobutyl-(3S)-[N-hydroxycarboxamido]-hexanoic acid amide of (1N)-carbomethoxymethyl-caprolactam-(3S) -amine (15). The benzyl hydroxamic acid 88 (176 mg, 0.351 mmole) is taken in 1 mL of 95% EtOH and the mixture is charged with 30 mg of 10% palladium on carbon and stirred under one atmosphere of hydrogen for hours. The mixture is then filtered through celite and concentrated to give 15.

EXAMPLE 16

(2R)-Isobutyl-(3S)-[N-hydroxycarboxamido]-6-hydroxyhexanoic acid amide of (1N)-carbomethoxymethyl-caprolactam-(3S)-amine (16)

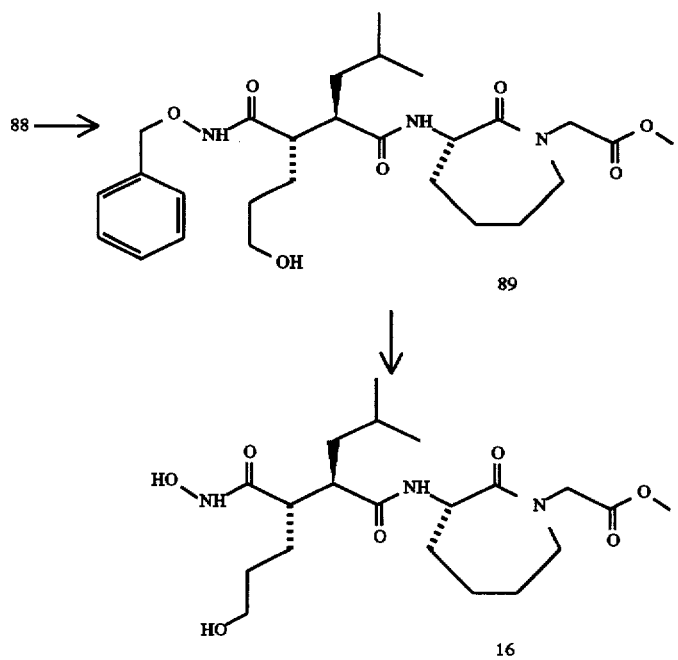

(2R)-Isobutyl-(3S)-[O-benzyl-N-hydroxycarboxamido]-6-hydroxyhexanoic acid amide of (1N)- carbomethoxymethyl-caprolactam-(3S)-amine (89). The starting olefin 88 (3R:3S=~1:1; 240 mg, 0.479 mmol) is taken in 5 mL of dry THF under argon and cooled to 0° C. at which time 9-borabicyclononane ("9-BBN") (3.45 mL, 0.5M in THF, 1.73 mmol) is added via syringe and the solution is stirred at 0° C. for 2 hr at which time NaOH (2 mL, 1M) and $H_2O_2$ (2 mL, 30%) are added and the resulting solution stirred for 5 min. The mixture is then partitioned between EtOAc and water and the organic layer is washed with sat. $NH_4Cl$ and brine, dried over $MgSO_4$, filtered and evaporated to give a crude oil. This diastereomeric mixture is chromatographed 2x over flash silica with EtOAc:EtOH (20:1) to give the 1S-89.

(2R)-Isobutyl-(3S)-[N-hydroxycarboxamido]-6-hydroxyhexanoic acid amide of (1N)-carbomethoxymethyl-caprolactam-(3S)-amine (16). The benzyl hydroxamic acid 89 (45 mg, 0.351 mmole) is taken in 1 mL of 95% EtOH and the mixture is charged with 10 mg of 10% palladium on carbon and stirred under one atmosphere of hydrogen for 12 hours. The mixture is then filtered through celite and concentrated to give 16.

EXAMPLE 17

Synthesis of (2R)-[(1S)-N-hydroxycarboxamido]-ethyldecanoic acid amide of 1N-(carbomethoxy-methyl)-caprolactam-(3S)-amine (17)

EXAMPLE 18

Synthesis of (2R)-[(1R)-N-hydroxycarboxamido]-ethyldecanoic acid amide of 1N-(carbomethoxy-methyl)-caprolactam-(3S)-amine (18)

warm to 0° C. and then recooled to –78° C. Methyl iodide (1.08 mL, 17.3 mmole) is then added slowly via syringe and the resulting mixture is stirred for 2 hr at –78° C. and 30 min. at 0° C., at which time the reaction is quenched with saturated $NH_4Cl$, partitioned between EtOAc and water and layers separated. The organic layer is washed with $NH_4Cl$, and brine, dried over $MgSO_4$, filtered and evaporated to give 5.81 g of crude oil which is chromatographed over flash silica with hexane:EtOAc (2:1) to give 90.

(2R)-[(1R)-Carbo-tert-Butoxy]-ethyl decanoic acid (91). The predominately (1R) acid 90 (1R:1S=8:1, 5 g, 15.7 mmole) is dissolved in 5 mL of dry THF under an argon atmosphere and cooled to –78° C. At which time lithium diisopropylamine (47 mL, 2M in THF, 47 mmole) is added via syringe and the mixture is stirred for 16 hr at –78° C. to 22° C. as the dry ice-acetone bath warmed to room temperature. The mixture is then recooled to –78° C., quenched with 15 mL of methanol (78 mmole) and poured into $NH_4Cl$. After warming up to room temperature, the reaction mixture is partitioned between EtOAc and water and layers separated. The organic layer is washed with 1N HCl, and brine, dried over $MgSO_4$, filtered and evaporated to give 5.81 g of crude oil which is chromatographed over flash silica with hexane:EtOAc (2:1) to give 91 (1S:1R=2:3).

(2R)-[(1R, S)Carbo-tert-butoxy]-ethyldecanoic acid amide of 1N-(carbomethoxy-methyl)-caprolactam-(3S)-amine (92). A mixture of acids 91 (1R:1S=3:2, 1.5 g, 5.00 mmole), the amine 55 (1.5 g, 7.50 mmole) and HOBT (1.53 g, 10.00 mmole) in 10 mL of DMF and 1.1 mL of NMM is charged with EDAC (1.15 mg, 6.00 mmole) and the reaction is stirred for 15 hr at room temperature. The reaction is then partitioned between water and EtOAc. The organic layer is

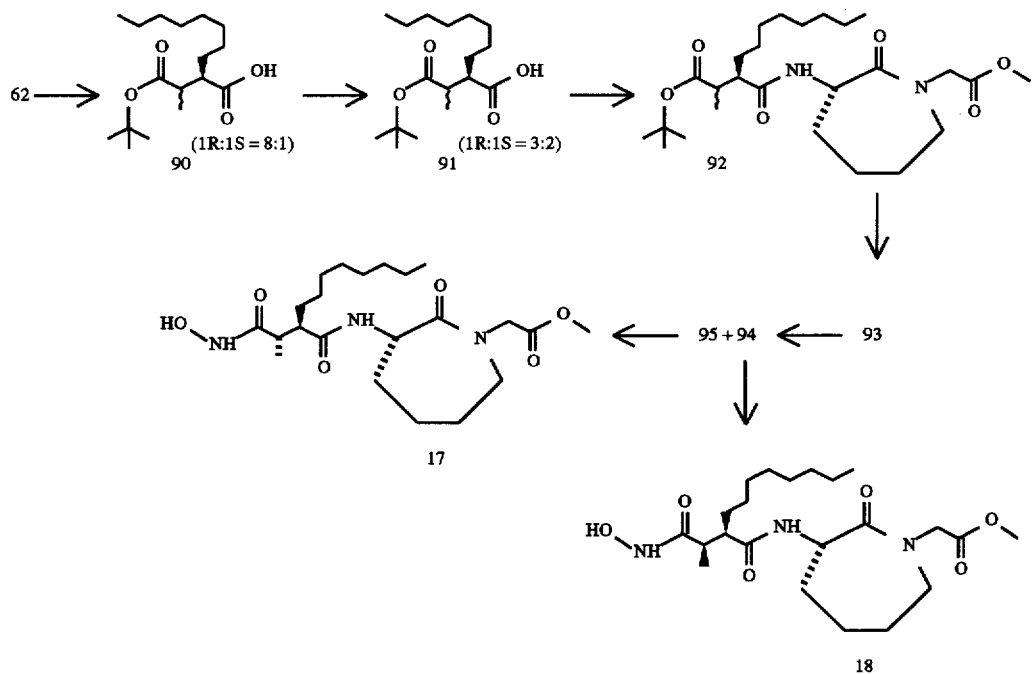

washed with 1N HCl, $NaHCO_3$, and brine, dried over $MgSO_4$, filtered and evaporated to a crude solid which is chromatographed over flash silica with hexanes:EtOAc (1:1) to give 92 (1R:1S=3:2).

(2R)-[(1R)-O-Benzyl-N-hydroxycarboxamido]-ethyldecanoic acid amide of 1N-(carbomethoxymethyl)-

(2R)-[(1R)-Carbo-tert-Butoxy]-ethyl decanoic acid (90). The starting acid 62 (4.5 g, 15.73 mmole) is dissolved in 5 mL of dry THF under an argon atmosphere and cooled to –78° C. at which time lithium hexamethyldisilazane (39.3 mL, 1M in THF, 39.3 mmole) is added via syringe and the mixture is stirred for 20 min. The mixture is allowed to caprolactam-(3S)-amine (94). (2R)-[(1S)-O-Benzyl-N-hydroxy- carboxamido]-ethyldecanoic acid amide of 1N-(carbomethoxymethyl)-caprolactam-(3 S)-amine (95). The esters 92 (1R:1S=3:2, 1.40 g, 2.90 mmole), are dissolved in 7 mL of $CH_2Cl_2$ under argon and to this mixture is added 7 mL of trifluoroacetic acid via syringe. The mixture is stirred for 2 hr at which time the mixture is concentrated to give 93.

A mixture of the resulting crude acid 93 (1.27 g, 2.86 mmole), O-benzyl hydroxylmine hydrochloride (456 mg, 2.86 mmole) and HOBT (875 mg. 572 mmole) in 5 mL of DMF and 941 µL of NMM is charged with EDAC (658 mg, 3.43 mmole) and the reaction is stirred for 15 hr at room temperature. The reaction is then partitioned between water

EXAMPLE 20

Synthesis of (2R)-[(1R)-N-Hydroxycarboxamido]-ethyl decanoic acid amide of N-[(2-methoxy)ethyl]-caprolactam-(3S)-amine (20)

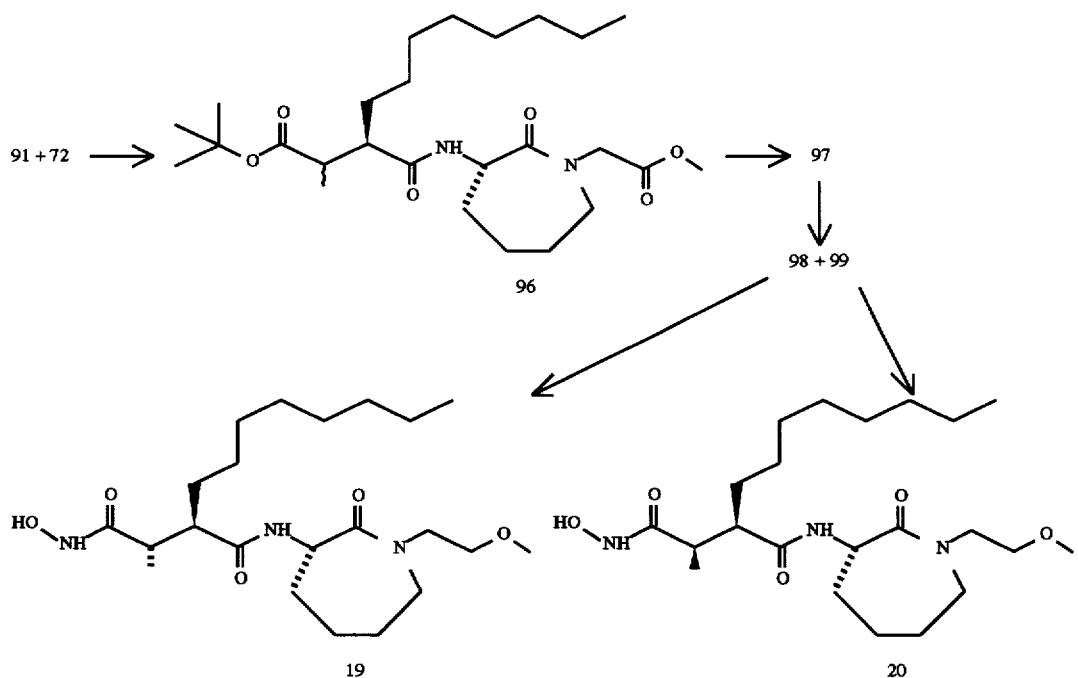

and EtOAc. The organic layer is then washed with 1N HCl, $NaHCO_3$, and brine, dried over $MgSO_4$, filtered and evaporated. The crude solid is then chromatographed through silica gel with hexanes:EtOAc (1:2) to give 94 and 95.

(2R)-[(1S)-N-hydroxycarboxamido]-ethyldecanoic acid amide of 1N-(carbomethoxy-methyl)-caprolactam-(3S)-amine (17). The benzyl hydroxamic acid 95 (260 mg, 0.489 mmole) is taken in 6 mL EtOH and the mixture is charged with 10% palladium on carbon (60 mg) and stirred under one atmosphere of hydrogen for 45 min. The mixture is then filtered through celite, concentrated and then recrystallized from EtOAc to give 17.

(2R)-[(1R)-N-hydroxycarboxamido]-ethyldecanoic acid amide of 1N-(carbomethoxy-methyl)-caprolactam-(3S)-amine (18). The benzyl hydroxamic acid 94 (300 mg, 0.565 mmole) is taken in 6 mL of EtOH and the mixture is charged with 10% palladium on carbon (60 mg) and stirred under one atmosphere of hydrogen for 45 min. The mixture is then filtered through celite, concentrated and then recrystallized from EtOAc to give 18.

EXAMPLE 19

Synthesis of (2R)-[(1S)-N-Hydroxycarboxamido]-ethyl decanoic acid amide of N-[(2-methoxy)ethyl]-caprolactam-(3S)-amine (19)

(2R)-[(1R,S)-Tert-Butylcarboxy]-ethyl decanoic acid amide of N-[(2-methoxy)ethyl]-caprolactam-(3S)-amine (96). (3S)-Amino-N-[(2-methoxy)ethyl]-caprolactam 72 (2.0 g, 10.78 mmole) is mixed with the decanoic acid 91 (1.5 g, 5.2 mmole), HOBT (3.65 g, 27 mmole), EDAC (2.07 g, 10.8 mmole) in 15 mL of DMF and 3 mL (27 mmole) of NMM at 0° C., and stirred for 17 hr at room temperature. The reaction is then partitioned between water and EtOAc. The organic layer is washed with 1N HCl, $H_2O$, 1N NaOH, and brine, dried over $MgSO_4$, filtered and evaporated to give an oil which is chromatographed over flash silica with hexane:EtOAc (1:1) to give 96.

(2R)-[(1S)-O-Benzylhydroxycarboxamic]-ethyl decanoic acid amide of N-[(2-methoxy)ethyl]-caprolactam-(3S)-amine (98). (2R)-[(1S)-tert-butyl carboxy]-ethyl decanoic acid amide of N-[(2-methoxy)ethyl]-caprolactam-(3S)-amine 96 (1.95 g, 4.1 mmole) is dissolved in 20 mL of methylene chloride and cooled to 0° C., trifluoroacetic acid (20 mL) is added slowly. The mixture is stirred for 2 hr at room temperature and evaporated to give 97. A mixture of the crude acid 97 (2.3 g, 4.1 mmole), O-benzyl hydroxylamine hydrochloride (0.78 g, 4.92 mmole) and HOBT (1.66 g. 12.3 mmole) in 15 mL of DMF and 1.54 mL of NMM (14 mmole) is charged with EDAC (0.94 g, 4.92 mmole) and the reaction is stirred for 15 hr at room temperature. The reaction is then partitioned between water and EtOAc. The organic layer is washed with 1N HCl, 1N NaOH, and brine, dried over MgSO$_4$, filtered and evaporated to give an oil which is chromatographed over flash silica with EtOAc:CH$_2$Cl$_2$:CH$_3$OH=10:10:1) to give the desired product as a diastereomeric mixture (1R:1S=3:2). Separation of single isomers is achieved by crystallization from EtOAc:hexane (3:2) to give 1S-98.

(2R)-[(1R)-O-Benzylhydroxycarboxamic]-ethyl decanoic acid amide of N-[(2-methoxy)ethyl]-caprolactam-(3S)-amine (99). The mother liquor is concentrated to give R-99.

(2R)-[(1S)-N-Hydroxycarboxamido]-ethyl decanoic acid amide of N-[(2-methoxy)ethyl]-caprolactam-(3S)-amine (19). The benzyl hydroxamic acid 98 (280 mg, 0.54 mmole) is taken in 8 mL of EtOH and the mixture is charged with 10% palladium on carbon (28 mg) and stirred under one atmosphere of hydrogen for 2 hr. The mixture is filtered through celite and concentrated to give a solid, which is purified by crystallization from EtOAc:CH$_3$OH (10:1) to give 19.

(2R)-[(1R)-N-Hydroxycarboxamido]-ethyl decanoic acid amide of N-[(2-methoxy)ethyl]-caprolactam-(3S)-amine (20). The benzyl hydroxamic acid 99 (670 mg, 1.3 mmole) is taken in 10 mL of EtOH and the mixture is charged with 10% palladium on carbon (66 mg) and stirred under one atmosphere of hydrogen for 3.5 hr. The mixture is filtered through celite and concentrated to give a solid, which is purified by crystallization from EtOAc to give 20.

EXAMPLE 21

Synthesis of (2R)-Isobutyl-3-(N-hydroxycarboxamido)-propanoic acid amide of N-(carbomethoxymethyl)-valerolactam-(3S)-amine carbon, filtered and concentrated to a solid 101. The compound is used without purification.

(3S)-tert-Butoxycarbonylamino valerolactam (102). (3S)-Amino-valerolactam (crude, 10.1 g, 88.4 mmole) is mixed with di-tert-butyl-dicarbonate 101 (19.9 g, 88.4 mmole) in 50 mL of methyl sulfoxide. The mixture is stirred overnight. The reaction is then partitioned between water and EtOAc. The organic layer is then washed with 0.1N HCl, H$_2$O, and brine, dried over MgSO$_4$, filtered and evaporated to give an oil which is chromatographed over flash silica with hexanes:EtOAc (1:1) to give 102.

3S)-tert-Butoxycarbonylamino-N-carbomethoxymethyl-valerolactam (103). (3S)-tert-Butoxycarbonylamino valerolactam 102 (1.85 g, 8.63 mmole) is dissolved in THF (5 mL) and cooled to −78° C. Lithium bis(trimethylsilyl)amide (11 mL, 10.4 mmole, 1M in THF) is added dropwise. After 10 min, methyl bromoacetate (1.1 mL, 11.2 mmole) is added. The resulting mixture is stirred at −78° C. for 2 hr, and at room temperature for 1 hr. The reaction is quenched with NH$_4$Cl, extracted by ethyl acetate. The organic layer is then washed with 0.1N HCl, H$_2$O, and brine, dried over MgSO$_4$, filtered and evaporated to give an oil which is chromatographed over flash silica with hexanes:EtOAc (1:1) to give 103.

[(2R)-Isobutyl-3-carbo-tert-butoxy]-propanoic acid amide of N-carbomethoxymethyl-valerolactam-(3S)-amine (105). (3S)-tert-Butoxycarbonylamino-N-carbomethoxymethyl-valerolactam 103 (2.1 g, 7.3 mmole) is dissolved in 20 mL of methylene chloride, trifluoroacetic acid (20 mL) is added slowly. The mixture is stirred for 2 hr and evaporated to give 104. The valerolactam amine 104 is mixed with (2R)-isobutyl-3-carbo-tert-butoxy-propanoic acid 23 (2.52 g, 11 mmole), HOBT (3.0 g, 21.9 mmole),

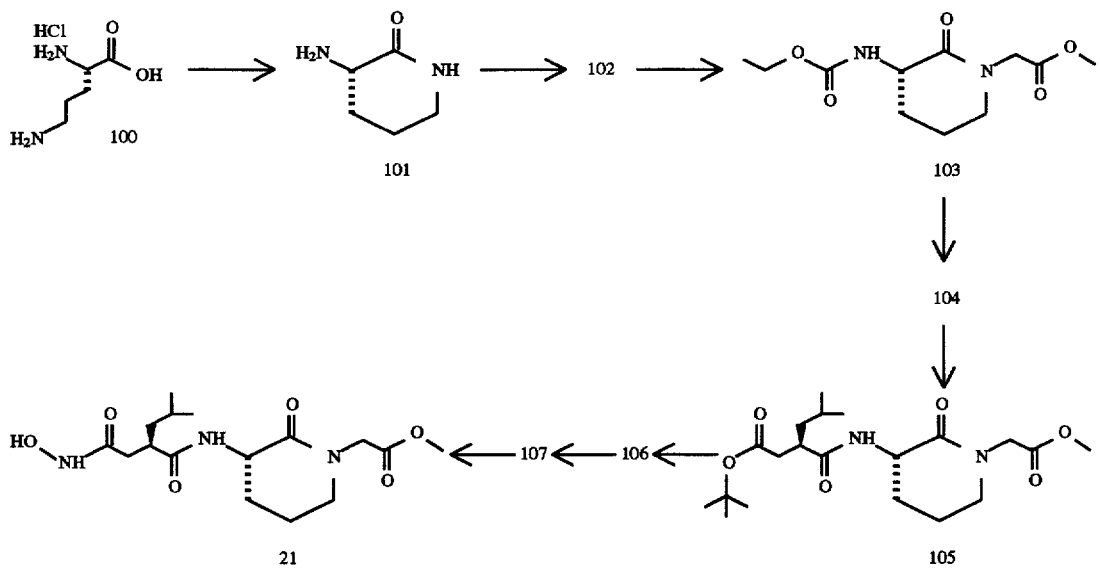

(3S)-Amino-valerolactam (101). To a 1 L 3 neck round bottom flask equipped with a condenser, thermometer, magnetic stirrer and argon inlet, is added L-ornithine hydrochloride 100 (15 g, 89 mmole), acetonitrile (280 mL) and hexamethyldisilazane (100 mL, 620 mmole). The mixture is heated to reflux for two days, then cooled to room temperature and poured into 500 mL of methanol. The solvents are removed by rotary evaporation. The residue is taken up in 250 mL of methylene chloride, then treated with activated EDAC (2.1 g, 11 mmole) in 10 mL of DMF and 4.2 mL (29.2 mmole) of triethylamine at 0° C., and stirred for 15 hr at room temperature. The reaction is then partitioned between water and EtOAc. The organic layer is then washed with 1N HCl, NaHCO$_3$, and brine, dried over MgSO$_4$, filtered and evaporated to give an oil which is chromatographed over flash silica with EtOAc to give 105.

[(2R)-Isobutyl-3-(O-benzyl-N-hydroxycarboxamido)]-propanoic acid amide of N-(carbomethoxymethyl)- valerolactam-(3S)-amine (107). [(2R)-Isobutyl-3-tert-butyl-carboxy]-propanoic acid amide of N-carbomethoxymethyl-valerolactam-(3S)-amine 105 (2.2 g, 5.5 mmole) is dissolved in 10 mL of methylene chloride and trifluoroacetic acid (10 mL) is added slowly. The mixture is stirred for 2 hr and evaporated to give 106. A mixture of the crude acid 106 (2.8 g, 5.5 mmole), O-benzyl hydroxylamine hydrochloride (1.96 g, 12.3 mmole) and HOBT (3.3 g, 24.6 mmole) in 10 mL of DMF and 2 mL of NMM (28.7 mmole) is charged with EDAC (2.0 g, 10.7 mmole) and the reaction is stirred for 15 hr at room temperature. The reaction is then partitioned between water and EtOAc. The organic layer is then washed with 1N HCl, NaHCO₃, and brine, dried over MgSO₄, filtered and evaporated to give an oil which chromatographed over flash silica with hexanes:EtOAc (1:1→1:4) to give 107.

(2R)-Isobutyl-3-(N-hydroxycarboxamido)-propanoic acid amide of N-(carbomethoyxymethyl)-valerolactam-(3S) -amine (21). The benzyl hydroxamic acid 107 (850 mg, 1.90 mmole) is taken in 10 mL EtOH and the mixture is charged with 10% palladium on carbon (85 mg) and stirred under one atmosphere of hydrogen for 1 hr. The mixture is then filtered through celite and concentrated to an oil. The crude product is purified on a silica gel column using 2% formic acid in ethyl acetate as the eluent to give 21.

EXAMPLE 22

Synthesis of [(2R)-Isobutyl-3-(N-hydroxylcarboxamido)] -propanoic acid amide of 2-oxo-3-amino-N-(carbomethoxymethyl)-pyridinone (22)

celite and concentrated to an oil. The crude product is chromatographed over flash silica with hexane:ethyl acetate (1:1 to 100% EtOAc) to give 110.

[(2R)-Isobutyl-3-carbo-tert-butoxy-propanoic acid amide of 2-oxo-3-amino-N-(carbomethoxymethyl)-pyridinone (111). The acid 23 (2.5 g, 11 mmole) is dissolved in 15 mL of THF and cooled to −15° C. NMM (1.3 mL, 11 mmole) and isobutylchloroformate (11 mmole, 1.6 mL) are added. After stirring for 30 min., NMM (1.3 mL, 11 mmole) and 110 (2.0 g, 11 mmole) are added. The reaction mixture is stirred for 17 hr and then quenched with 1N HCl and extracted with EtOAc. The organic layer is washed with 1N HCl, NaHCO₃, and brine, dried over MgSO₄, filtered and evaporated to give an oil which is chromatographed over flash silica with EtOAc to give 111.

[(2R)-Isobutyl-3-O-Benzylhydroxylcarboxamido]-propanoic acid amide of 2-oxo-3-amino-N-(carbomethoxymethyl)-pyridinone (113). The ester 111 (0.8 g, 2 mmole) is dissolved in 5 mL of methylene chloride and trifluoroacetic acid (5 mL) is added slowly at 0° C. The mixture is stirred for 2 hr and evaporated to give 112. The crude acid 112 is mixed with O-benzylhydroxylamine hydrochloride (0.5 g, 3.0 mmole), HOBT (0.81 g, 6 mmole), EDAC (0.58 g, 3 mmole) in 10 mL of DMF and 0.77 mL (7 mmole) of NMM at 0° C., and stirred for 17 hr at room temperature. The reaction is then partitioned between water and EtOAc. The organic layer is then washed with 1N HCl, NaHCO₃, and brine, dried over MgSO₄, filtered and evaporated to give an oil which is chromatographed over flash silica with hexane:EtOAc (2:3 to 1:4) to give 113.

[(2R)-Isobutyl-3-(N-hydroxylcarboxamido)]-propanoic acid amide of 2-oxo-3-amino-N-(carbomethoxymethyl)-

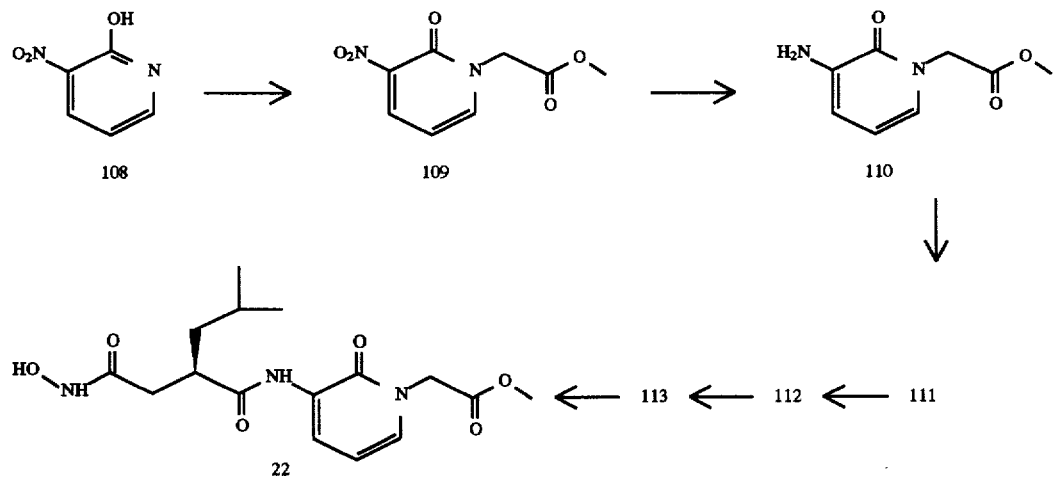

2-Oxo-3-nitro-N-(carbomethoxymethyl)-pyridinone (109). 2-Hydroxy-3-nitropyridine 108 (10 g, 71.38 mmole) is mixed with pulverized potassium carbonate (10.9 g, 78.5 mmole) and 30 mL of DMF. After 10 min, methyl bromoacetate (10.4 mL, 107 mmole) is added. The resulting mixture is stirred at room temperature for 4.5 hr. The reaction is quenched by water and extracted by ethyl acetate. The organic layer is then washed with brine, dried over MgSO₄, filtered and evaporated to give an oil which is chromatographed over flash silica with EtOAc to give 109.

2-Oxo-3-amino-N-(carbomethoxymethyl)-pyridinone (110). The pyridinone 109 (3.0 g, 14.1 mmole) is taken in 45 mL of EtOH and the mixture is charged with 10% palladium on carbon (0.3 g) and stirred under one atmosphere of hydrogen for 17 hr. The mixture is then filtered through pyridinone (22). The benzyl hydroxamic acid 113 (180 mg, 0.4 mmole) is taken in 5 mL of EtOH and the mixture is charged with 10% palladium on carbon (20 mg) and stirred under one atmosphere of hydrogen for 6 hours. TLC (EtOAc) indicates persistence of a small amount of starting material left. More palladium on carbon (18 mg) is added, 113 is and hydrogenated for another 20 min. The mixture is then filtered through celite and concentrated to give a semisolid, which is purified by preparative TLC (silica, EtOAc) to give 22.

Example A

A tablet composition for oral administration, according to the present invention, is made comprising:

| Component | Amount |
|---|---|
| •(2R)-[(1S)-N-Hydroxycarboxamido]-ethyl decanoic acid amide of N-[(2-methoxy)ethyl]-caprolactam-(3S)-amine[1] | 15. mg |
| •Lactose | 120. mg |
| •Maize Starch | 70. mg |
| •Talc | 4. mg |
| •Magnesium Stearate | 1. mg |

[1]The hydroxamic acid prepared according to Example 19. Other compounds having a structure to Formula (I) are used with substantially similar results.

Example B

A capsule for oral administration, according to the present invention, is made comprising:

| Component | Amount (% w/w) |
|---|---|
| •(2R)-[(1S)-N-hydroxycarboxamido]-ethyldecanoic acid amide of 1N-(carbomethoxy-methyl)-caprolactam-(3S)-amine[2] | 15% |
| •Polyethylene glycol | 85% |

[2]The hydroxamic acid prepared according to Example 17. Other compounds having a structure according to Formula (I) are used with substantially similar results.

Example C

A saline-based composition for local administration, according to the present invention, is made comprising:

| Component | Amount (% w/w) |
|---|---|
| •(2R)-Isobutyl-(3S)-[N-hydroxycarboxamido]-6-hydroxyhexanoic acid amide of (1N)-carbomethoxymethyl-caprolactam-(3S)-amine[3] | 10% |
| =Ethanol | 10% |
| •Saline | 80% |

[3]The hydroxamic acid prepared according to Example 16. Other compounds having a structure according to Formula (I) are used with substantially similar results.

Example D

A human female subject weighing 60 kg (132 lbs), suffering from rheumatoid arthritis, is treated by a method of this invention. Specifically, for 2 years, a tablet containing 50 mg of (2R)-N-hydroxycarboxamidemethyldecanoic acid amide of 1N-(carbomethoxy-methyl)-caprolactam-(3S)-amine (prepared according to Example 9) is administered orally to said subject.

At the end of the treatment period, the patient is examined and is found to have reduced intimation, and improved mobility without concomitant pain.

Other compounds having a structure according to Formula (I) are used with substantially similar results.

Example E

A human male subject weighing 90 kg (198 lbs), suffering from osteoarthrits, is treated by a method of this invention. Specifically, for 5 years, a capsule containing 70 mg of (2R)-Isobutyl-3-(N-hydroxycarboxamido)-propanoic acid amide of N-(carbomethoxymethyl)-valerolactam-(3S)-amine (made according to Example 21) is administered daily to said subject.

At the end of the treatment period, the patient is examined via orthoscopy, and found to have no further advancement of erosion/fibrillation of the articular cartilage.

Other compounds having a structure according to Formula I are used with substantially similar results.

Example F

A human male subject weighing 90 kg (198 lbs), suffering from corneal ulcerations, is treated by a method of this invention. Specifically, for 2 months, a saline solution containing 10 mg of (2R)-N-Hydroxycarboxamidomethyl heptanoic acid amide of N-(carbomethoxymethyl)-caprolactam-(3S)-amine (made according to Example 8) is administered to said subject's affected eye twice-daily.

Other compounds having a structure according to Formula I are used with substantially similar results.

What is claimed is:

1. A compound selected from:

(2R)-Isobutyl-3-(N-hydroxycarboxamido)-propanoic acid amide of 1N-(carbomethoxy-methyl)-caprolactam-(3S)-amine;

(2R)-Isobutyl-3-(N-hydroxycarboxamido)-propionic acid amide of 1N-(methyl-carboxamidomethyl)-caprolactam-(3S)-amine;

(2R)-Isobutyl-3-(N-hydroxycarboxamido)-propionic acid amide of 1N-(carbo-tert-butoxy-methyl)-caprolactam-(3S)-amine;

(2R)-Isobutyl-3-(N-hydroxycarboxamido)-propionic acid amide of 1N-Benzyl-caprolactam-(3S)-amine;

(2R)-Isobutyl-3-N-hydroxycarboxamidopropionic acid amide of 1N-(carbo-benzyloxy-methyl)-caprolactam-(3S)-amine;

(2R)-Isobutyl-3-(N-hydroxycarboxamido)-propionic acid amide of 1N-(N-benzylcarboxamidomethyl)-caprolactam-(3S)-amine;

(2R)-Isobutyl-3-N-hydroxycarboxamidopropionic acid amide of 1N-(n-butyl-carboxamidomethyl)-caprolactam-(3S)-amine;

(2R)-N-Hydroxycarboxamidomethyl heptanoic acid amide of N-(carbomethoxymethyl)-caprolactam-(3S)-amine;

(2R)-N-hydroxycarboxamidemethyldecanoic acid amide of 1N-(carbomethoxymethyl)-caprolactam-(3S)-amine;

(2R)-N-Hydroxycarboxamidomethyl decanoic acid amide of N-toluenesulfonyl-caprolactam-(3S)-amine;

(2R)-N-Hydroxycarboxamidomethyl decanoic acid amide of N-[(2-methoxy)ethyl]-caprolactam-(3S)-amine;

(2R)-N-Hydroxycarboxamidomethyl decanoic acid amide of 1N-n-butyl-caprolactam-(3S)-amine;

(2R)-Isobutyl-(3S)-[N-hydroxycarboxamido]-butanoic acid amide of (1N)-carbomethoxymethyl-caprolactam-(3S)-amine;

(2R)-Isobutyl-(3R)-[N-hydroxycarboxamido]-butanoic acid amide of (1N)-carbomethoxymethyl-caprolactam-(3S)-amine;

(2R)-Isobutyl-(3S)-[N-hydroxycarboxamido]-hexanoic acid amide of (1N)-carbomethoxymethyl-caprolactam-(3S)-amine;

(2R)-Isobutyl-(3S)-[N-hydroxycarboxamido]-6-hydroxyhexanoic acid amide of (1N)-carbomethoxymethyl-caprolactam-(3S)-amine;

(2R)-[(1S)-N-hydroxycarboxamido]-ethyldecanoic acid amide of 1N-(carbomethoxy-methyl)-caprolactam-(3S)-amine;

(2R)-[(1R)-N-hydroxycarboxamido]-ethyldecanoic acid amide of 1N-(carbomethoxy-methyl)-caprolactam-(3S)-amine;

(2R)-[(1S)-N-Hydroxycarboxamido]-ethyldecanoic acid amide of N-[(2-methoxy)ethyl]-caprolactam-(3S)-amine;

(2R)-[(1R)-N-Hydroxycarboxamido]-ethyldecanoic acid amide of N-[(2-methoxy)ethyl]-caprolactam-(3S)-amine;

(2R)-Isobutyl-3-(N-hydroxycarboxamido)-propanoic acid amide of N-(carbomethoxymethyl)-valerolactam-(3S)-amine; and

[(2R)-Isobutyl-3-(N-hydroxylcarboxamido)]-propanoic acid amide of 2-oxo-3-amino-N-(carbomethoxymethyl)-pyridinone.

2. A method for preventing or treating a disease associated with unwanted matrixmetalloprotease activity in a human or other animal subject, the method comprising administering to said subject a safe and effective mound of a compound of claim 1.

* * * * *